United States Patent
Saito

(10) Patent No.: US 8,535,221 B2
(45) Date of Patent: Sep. 17, 2013

(54) ELECTRONIC ENDOSCOPE SYSTEM AND METHOD FOR OBTAINING VASCULAR INFORMATION

(75) Inventor: Takaaki Saito, Kanagawa (JP)

(73) Assignee: FujiFilm Corporation, Tokyo (JP)

( * ) Notice: Subject to any disclaimer, the term of this patent is extended or adjusted under 35 U.S.C. 154(b) by 203 days.

(21) Appl. No.: 13/216,171

(22) Filed: Aug. 23, 2011

(65) Prior Publication Data

US 2012/0053434 A1 Mar. 1, 2012

(30) Foreign Application Priority Data

Aug. 24, 2010 (JP) ................................ 2010-187213

(51) Int. Cl.
  *A61B 1/04* (2006.01)
  *A61B 1/06* (2006.01)
  *A61B 5/00* (2006.01)
(52) U.S. Cl.
  USPC ........... 600/180; 600/109; 600/118; 600/178; 600/339
(58) Field of Classification Search
  USPC ................ 600/109, 118, 178, 180, 476, 477, 600/323, 324, 325, 339
  See application file for complete search history.

(56) References Cited

U.S. PATENT DOCUMENTS

| | | | | |
|---|---|---|---|---|
| 7,450,159 B2 * | 11/2008 | Imaizumi et al. | ........... | 348/222.1 |
| 7,539,335 B2 * | 5/2009 | Fukuyama | ..................... | 382/128 |
| 7,711,403 B2 * | 5/2010 | Jay et al. | ........................ | 600/407 |
| 2003/0176768 A1 * | 9/2003 | Gono et al. | .................... | 600/109 |
| 2008/0294105 A1 * | 11/2008 | Gono et al. | .................... | 604/109 |
| 2008/0306343 A1 * | 12/2008 | Yamazaki | ..................... | 600/180 |
| 2011/0071353 A1 * | 3/2011 | Ozawa et al. | ................. | 600/109 |
| 2011/0077462 A1 * | 3/2011 | Saitou et al. | ................. | 600/109 |
| 2011/0230715 A1 * | 9/2011 | Saito | ............................ | 600/109 |
| 2011/0237882 A1 * | 9/2011 | Saito | ............................ | 600/109 |
| 2011/0237883 A1 * | 9/2011 | Chun | ........................... | 600/109 |
| 2011/0237884 A1 * | 9/2011 | Saito | ............................ | 600/109 |
| 2011/0237895 A1 * | 9/2011 | Yoshida et al. | ............... | 600/180 |
| 2011/0245642 A1 * | 10/2011 | Minetoma | ..................... | 600/324 |
| 2011/0301443 A1 * | 12/2011 | Yamaguchi et al. | .......... | 600/324 |
| 2011/0319711 A1 * | 12/2011 | Yamaguchi et al. | .......... | 600/109 |

FOREIGN PATENT DOCUMENTS

| | | |
|---|---|---|
| JP | 2648494 (B2) | 5/1997 |
| JP | 2002-34893 (A) | 2/2002 |

* cited by examiner

*Primary Examiner* — John P Leubecker
(74) *Attorney, Agent, or Firm* — McGinn IP Law Group, PLLC

(57) ABSTRACT

First to third lights are applied to a body cavity from a light source. The first and second lights have different wavelength ranges. Each of the first and second lights varies in absorbance in accordance with oxygen saturation of hemoglobin. The third light is a reference light used for comparison with the first and second lights. A monitoring section monitors a first light quantity ratio between the first and third lights and a second light quantity ratio between the second and third lights. A controller controls the light source such that first and second light quantity ratios reach their respective standard values. First to third data are obtained from images captured with illumination of the three lights, respectively. Vessel depth information and oxygen saturation information are obtained simultaneously from a first brightness ratio between the first and third data and a second brightness ratio between the second and third data.

17 Claims, 12 Drawing Sheets

ELECTRONIC ENDOSCOPE SYSTEM AND METHOD FOR OBTAINING VASCULAR INFORMATION

BACKGROUND OF THE INVENTION

1. Field of the Invention

The present invention relates to an electronic endoscope system for obtaining vascular information from an image captured with an electronic endoscope and a method for obtaining the vascular information.

2. Description Related to the Prior Art

Diagnoses and treatments using an electronic endoscope are very common. The electronic endoscope is provided with a long insert section to be inserted into a patient's body cavity. The insert section incorporates an imaging device such as a CCD in its distal end portion. The electronic endoscope is connected to a light source apparatus. Light emitted from the light source apparatus is applied to the patient's body cavity through the distal end portion of the insert section. The imaging device in the distal end portion captures an image of an objective tissue in the body cavity while the light illuminates the body cavity. The captured image is subjected to various processes performed by the processing apparatus connected to the electronic endoscope, and then displayed on a monitor. The electronic endoscope allows an operator to observe an image of the patient's body cavity real-time, which ensures accurate diagnosis.

A white light source such as a xenon lamp is used as the light source apparatus. The xenon lamp emits white broadband light in a wavelength range from a blue region to a red region. Illuminating the body cavity with the white broadband light provides an image showing an outline of an objective tissue. However, it is difficult to clearly observe microblood vessels, deep blood vessels, a pit pattern, an uneven structure such as a recess and a protrusion. It is known that illumination of narrowband light with a wavelength limited to a specific region allows clear observation of the above body sites. It is known that various pieces of information, such as oxygen saturation of hemoglobin in a blood vessel on an objective tissue, are obtained from image data when an image is captured with the illumination of the narrowband light.

For example, in U.S. Patent Application Publication No. 2003/0176768 (corresponding to Japanese Patent No. 3559755), three kinds of narrowband lights (red, green, and blue lights) are sequentially applied to a patient's body cavity as the illumination light. During the application of each narrowband light, an image is captured. Light reaches a deeper blood vessel as its wavelength becomes longer. For example, when the blue illumination light is applied, an image is captured with its surface blood vessel emphasized. When the green illumination light is applied, an image is captured with its middle blood vessel emphasized. When the blue illumination light is applied, an image is captured with its deep blood vessel emphasized. Color image processing is performed based on the image data of each of the captured images. Accordingly, in an image produced, the surface blood vessel, the middle blood vessel, and the deep blood vessel are shown in different colors so as to be easily distinguished from each other.

In Japanese Patent No. 2648494, narrowband lights IR1, IR2, and IR3 in a near infrared region are applied. The application of the narrowband lights IR1 and IR3 changes hemoglobin absorbance of a blood vessel due to oxygen saturation. The application of the narrowband light IR2 does not change the hemoglobin absorbance. During the application of each narrowband light as the illumination light, an image is captured. Changes in brightness of the images are calculated based on the images captured with the applications of the narrowband lights IR1 and IR3 and the image captured with the application of the narrowband light IR2. The calculated changes in brightness are reflected in black-and-white or in pseudo-color to the image. The information on the oxygen saturation of hemoglobin in the blood vessel is obtained from the image.

Recently, it has been desired to perform diagnosis and the like while the vessel depth and the oxygen saturation are obtained simultaneously. The hemoglobin absorbance of a blood vessel, however, changes considerably in accordance with a wavelength of the light applied (see FIG. 3). Accordingly, it is difficult to obtain information on both the vessel depth and the oxygen saturation simultaneously.

The sequential application of the three kinds of narrowband lights (the red, green, and blue lights) provides information on the depth of a blood vessel as described in the U.S. Patent Application Publication No. 2003/0176768, for example. However, the application of three kinds of narrowband lights does not provide information on the oxygen saturation. On the other hand, the application of the narrowband light IR1, IR2, and IR3 in a near infrared region provides information on the oxygen saturation as described in the Japanese Patent No. 2648494. However, the application of narrowband lights in the near infrared region does not provide the information on the depth of the blood vessel. The information on the vessel depth and the information on the oxygen saturation cannot be obtained simultaneously even if the lights in wavelength regions including both of the wavelength regions disclosed in the U.S. Patent Application Publication No. 2003/0176768 and the Japanese Patent No. 2648494 are applied.

SUMMARY OF THE INVENTION

An object of the present invention is to provide an electronic endoscope system and a method for obtaining vascular information capable of obtaining blood depth information and oxygen saturation information simultaneously.

In order to achieve the above and other objects, an electronic endoscope system of the present invention includes an electronic endoscope, an illumination section, a controller, a signal obtaining section, and a vascular information obtaining section. The electronic endoscope has an image sensor to capture an image of an objective tissue including a blood vessel. The illumination section applies first to third illumination lights to the objective tissue. The first and second illumination lights have different wavelength ranges from each other and vary in absorbance in accordance with oxygen saturation of hemoglobin in the blood vessel. The third illumination light is a reference light used for comparison with the first and second illumination lights. The controller controls light quantities of the first to third illumination lights based on a first light quantity ratio between the light quantities of the first and third illumination lights and a second light quantity ratio between the light quantities of the second and third illumination lights. The signal obtaining section obtains first to third imaging signals outputted from the image sensor. The first to third imaging signals corresponds to respective reflection light quantities of reflection lights from the objective tissue upon application of the first to third illumination lights. The vascular information obtaining section obtains vascular information, having both oxygen saturation information of the oxygen saturation and vessel depth information of the blood vessel, based on a first brightness ratio and a second brightness ratio. The first brightness ratio is a ratio between the first and third imaging signals. The second brightness ratio is a ratio between the second and third imaging signals.

The illumination section applies the first to third illumination lights sequentially or in any combination as necessary. It is preferable that the electronic endoscope system further includes a light quantity detector for detecting light quantities of the first to third illumination lights. It is preferable that the controller controls the light quantities of the first to third illumination lights based on detected light quantities such that the first and second light quantity ratios reach respective standard light quantity ratios. It is preferable that the first and second illumination lights are narrowband lights in a blue region. It is preferable that at least one of the first and second illumination lights has a center wavelength at or below 450 nm. It is preferable that in each of the wavelength ranges of the first and second illumination lights, magnitude relation between absorbance of deoxyhemoglobin and absorbance of oxyhemoglobin is reversed in respective absorption spectra. It is preferable that the wavelength range of the first illumination light is 440±10 nm and the wavelength range of the second illumination light is 470±10 nm. It is preferable that the electronic endoscope system further includes a memory for storing the light quantities of the first to third illumination light and first to third image data. The light quantities of the first and third illumination lights are associated with the first to third image data, respectively. The first to third image data are generated based on the first to third imaging signals, respectively.

It is preferable that the electronic endoscope system further includes a calibration imaging signal obtaining section and a difference value storage. The calibration imaging signal obtaining section obtains first to third calibration imaging signals outputted from the image sensor in accordance with respective reflection light quantities of lights reflected by a reference object upon application of the first to third illumination lights. The reference object has a known reflection spectrum. The difference value storage stores a difference value between a first imaging signal ratio and its corresponding standard imaging signal ratio and a difference value between the second imaging signal ratio and its corresponding standard imaging signal ratio. The difference values are calculated based on the first and second imaging signal ratios. The first imaging signal ratio is a ratio between the first and third calibration imaging signals and corresponds to the first light quantity ratio. The second imaging signal ratio is a ratio between the second and third calibration imaging signals and corresponds to the second light quantity ratio. The controller controls the light quantities of the first to third illumination lights based on the difference values.

Another electronic endoscope system of the present invention includes an electronic endoscope, an illumination section, a signal obtaining section, a signal correcting section, and a vascular information obtaining section. The electronic endoscope has an image sensor for capturing an image of an objective tissue including a blood vessel. The illumination section applies a first illumination light, a second illumination light, and a third illumination light to the objective tissue. The first and second illumination lights have different wavelength ranges from each other. Each of the first and second illumination lights varies in absorbance in accordance with oxygen saturation of hemoglobin in the blood vessel. A third illumination light is a reference light used for comparison with the first and second illumination lights. The signal obtaining section obtains a first imaging signal, a second imaging signal, and a third imaging signal. The first to third imaging signals are outputted from the image sensor in accordance with respective reflection light quantities of reflection lights from the objective tissue upon application of the first to third illumination lights. The signal correcting section for correcting the first to third imaging signals based on a first light quantity ratio between the light quantities of the first and third illumination lights and a second light quantity ratio between the light quantities of the second and third illumination lights. The vascular information obtaining section obtains vascular information, having both oxygen saturation information of the oxygen saturation and vessel depth information of the blood vessel, based on a first brightness ratio and a second brightness ratio. The first brightness ratio is a ratio between a corrected first imaging signal and a corrected third imaging signal. The second brightness ratio is a ratio between a corrected second imaging signal and a corrected third imaging signal.

The illumination section applies the first to third illumination lights sequentially or in any combination as necessary. It is preferable that the electronic endoscope system further includes a light quantity detector for detecting the light quantities of the first to third illumination lights, and the signal correcting section corrects the first to third imaging signals based on a difference value between the first light quantity ratio and its corresponding standard light quantity ratio and a difference value between the second light quantity ratio and its corresponding standard light quantity ratio, and the difference values are calculated based on the light quantities detected by the light quantity detector, and the vascular information obtaining section obtains the vascular information based on the corrected first to third imaging signals.

It is preferable that the electronic endoscope system further includes a calibration imaging signal obtaining section and a difference value memory. The calibration imaging signal obtaining section obtains first to third calibration imaging signals outputted from the image sensor in accordance with respective reflection light quantities of lights reflected by a reference object upon application of the first to third illumination lights, the reference object having a known reflection spectrum. The difference value memory stores a difference value between a first imaging signal ratio and its corresponding standard imaging signal ratio and a difference value between the second imaging signal ratio and its corresponding standard imaging signal ratio. The difference values is calculated based on the first and second imaging signal ratios. The first imaging signal ratio is a ratio between the first and third calibration imaging signals and corresponds to the first light quantity ratio. The second imaging signal ratio is a ratio between the second and third calibration imaging signals and corresponds to the second light quantity ratio. The signal correcting section corrects the first to third imaging signals based on the difference values and the vascular information obtaining section obtains the vascular information based on corrected first to third imaging signals.

A method for obtaining vascular information includes an applying step, a controlling step, a signal obtaining step, and a vascular information obtaining step. In the applying step, first to third illumination lights are applied to an objective tissue having a blood vessel. The first and second illumination lights have different wavelength ranges from each other and vary in absorbance in accordance with oxygen saturation of hemoglobin in the blood vessel. The third illumination light is a reference light used for comparison with the first and second illumination lights. In the controlling step, light quantities of the first to third illumination lights are controlled based on a first light quantity ratio between light quantities of the first and third illumination lights and a second light quantity ratio between light quantities of the second and third illumination lights. In the signal obtaining step, first to third imaging signals outputted from the image sensor in accordance with respective reflection light quantities of lights reflected by the objective tissue are obtained upon application of the first to third illumination lights. In the vascular information obtaining step, vascular information, having both oxygen saturation information of the oxygen saturation and vessel depth information of the blood vessel, is obtained based on a first brightness ratio and a second brightness ratio. The first brightness ratio is a ratio between signal values of the first imaging signal and the third imaging signal. The second brightness ratio is a ratio between signal values of the second imaging signal and the third imaging signal.

The illumination section applies the first to third illumination lights sequentially or in any combination as necessary. It is preferable that the method further includes a detecting step in which light quantities of the first to third illumination lights are detected. In the controlling step, the light quantities of the first to third illumination lights are controlled such that the first light quantity ratio and the second light quantity ratio reach their respective standard light quantity ratios during the light quantity control.

It is preferable that the method further includes a calibration imaging signal obtaining step and a storing step. In the calibration imaging signal obtaining step, first to third calibration imaging signals outputted from the image sensor in accordance with respective reflection light quantities of lights reflected by a reference object upon application of the first to third illumination lights are obtained. The reference object has a known reflection spectrum. In the storing step, a difference value between a first imaging signal ratio and its corresponding standard imaging signal ratio and a difference value between the second imaging signal ratio and its corresponding standard imaging signal ratio are stored. The difference values are calculated based on the first and second imaging signal ratios. The first imaging signal ratio is a ratio between the first and third calibration imaging signals and corresponds to the first light quantity ratio. The second imaging signal ratio is a ratio between the second and third calibration imaging signals and corresponds to the second light quantity ratio.

Another method for obtaining vascular information according to the present invention includes an applying step, a signal obtaining step, a signal correction step, and vascular information obtaining step. In the applying step, first to third illumination lights are applied to an objective tissue having a blood vessel. The first and second illumination lights have different wavelength ranges from each other and vary in absorbance in accordance with oxygen saturation of hemoglobin in the blood vessel. The third illumination light is a reference light used for comparison with the first and second illumination lights. In the signal obtaining step, first to third imaging signals outputted from the image sensor are obtained. The first to third imaging signals correspond to respective reflection light quantities of reflection lights from the objective tissue upon application of the first and second illumination lights. In a signal correcting step, the first to third imaging signals are corrected based on a first light quantity ratio and a second light quantity ratio. The first light quantity ratio is a ratio between light quantities of the first and third illumination lights. The second light quantity ratio is a ratio between light quantities of the second and third illumination lights. In the vascular information obtaining step, vascular information is obtained based on a first brightness ratio and a second brightness ratio. The first brightness ratio is a ratio between signal values of a corrected first imaging signal and a corrected third imaging signal. The second brightness ratio is a ratio between signal values of a corrected second imaging signal and the corrected third imaging signal. The vascular information has both oxygen saturation information of the oxygen saturation and vessel depth information of the blood vessel.

The illumination section applies the first to third illumination lights sequentially or in any combination as necessary. It is preferable that the method further includes the detecting step and correcting step. In the detecting step, the light quantities of the first to third illumination lights are detected. In the correcting step, the first to third imaging signals are corrected based on a difference value between the first light quantity ratio and its corresponding standard light quantity ratio and a difference value between the second light quantity ratio and its corresponding standard light quantity ratio. The difference values are calculated based on the detected light quantities.

It is preferable that the method further includes a calibration imaging signal obtaining step and a storing step. In the calibration imaging step, first to third calibration imaging signals outputted from the image sensor in accordance with respective reflection light quantities of lights reflected by a reference object upon application of the first to third illumination lights are obtained. The reference object has a known reflection spectrum. In the storing step, a difference value between a first imaging signal ratio and its corresponding standard imaging signal ratio and a difference value between the second imaging signal ratio and its corresponding standard imaging signal ratio are stored. The difference value is calculated based on the first and second imaging signal ratios. The first imaging signal ratio is a ratio between the first and third calibration imaging signals and corresponds to the first light quantity ratio. The second imaging signal ratio is a ratio between the second and third calibration imaging signals and corresponds to the second light quantity ratio.

According to the present invention, the first to third illumination lights are applied. The first and second illumination lights have different wavelength ranges from each other. Each of the first and second illumination lights varies in absorbance in accordance with the oxygen saturation of hemoglobin in blood vessel. The third illumination light, being the reference light, is used for comparison with the first and second illumination lights. By the application of the first to third illumination lights, both the vessel depth information and oxygen saturation information are obtained simultaneously. By controlling the light quantities of the first to third illumination lights based on the first light quantity ratio between the light quantities of the first and third illumination lights and the second light quantity ratio between the light quantities of the second and third illumination lights, or by correcting the first to third imaging signals corresponding to the first to third illumination lights, the vessel depth information and the oxygen saturation information are determined with stability and unaffected by unstable light sources.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

Figure 1:
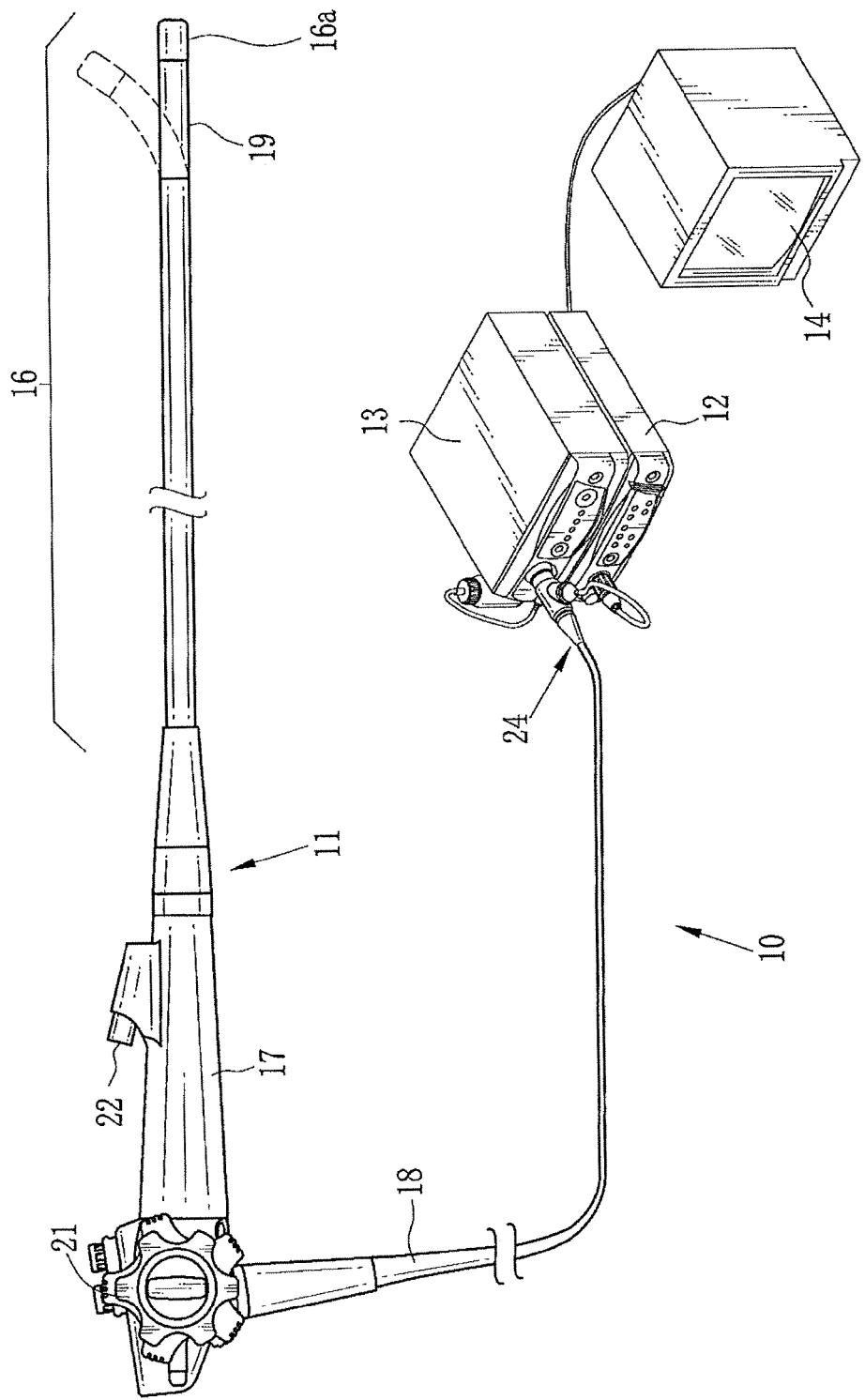
FIG. 1 is an external view of an electronic endoscope system according to a first embodiment of the present invention.

As shown in FIG. 1, an electronic endoscope system 10 according to a first embodiment of the present invention is provided with an electronic endoscope 11, a processing apparatus 12, a light source apparatus 13, and a monitor 14. The electronic endoscope 11 captures an image in a patient's body cavity. The processing apparatus 12 generates an image of an objective tissue (an object of interest) in the body cavity based on a signal obtained by the image capture. The light source apparatus 13 supplies light for illuminating the body cavity. The monitor 14 displays the image generated. The electronic endoscope 11 is provided with a flexible insert section 16 to be inserted into the body cavity, a handling section 17 provided in the basal portion of the insert section 16, and a universal cord 18. The universal cord 18 connects the handling section 17, the processing apparatus 12, and the light source apparatus 13. The processor apparatus 12 is provided with a console 23 (see FIG. 2) composed of a keyboard and a mouse for inputting an operation signal.

The insert section 16 has a bending portion 19 at its tip. The bending portion 19 has a plurality of joint pieces. Operating an angle knob 21 provided in the handling section 17 bends the bending portion 19 in horizontal and vertical directions. A distal portion 16a is provided at a distal end of the bending portion 19. The distal portion 16a incorporates an optical system and the like used for the image capture in the body cavity. Bending the bending portion 19 directs the distal portion 16a to a desired direction.

A connector 24 is attached to one end of the universal cord 18 where the processing apparatus 12 and the light source apparatus 13 are to be connected. The connector 24 is a multiple-type connector composed of a communication connector and a light source connector. The electronic endoscope 11 is detachably connected to the processing apparatus 12 and the light source apparatus 13 via the connector 24.

Figure 2:
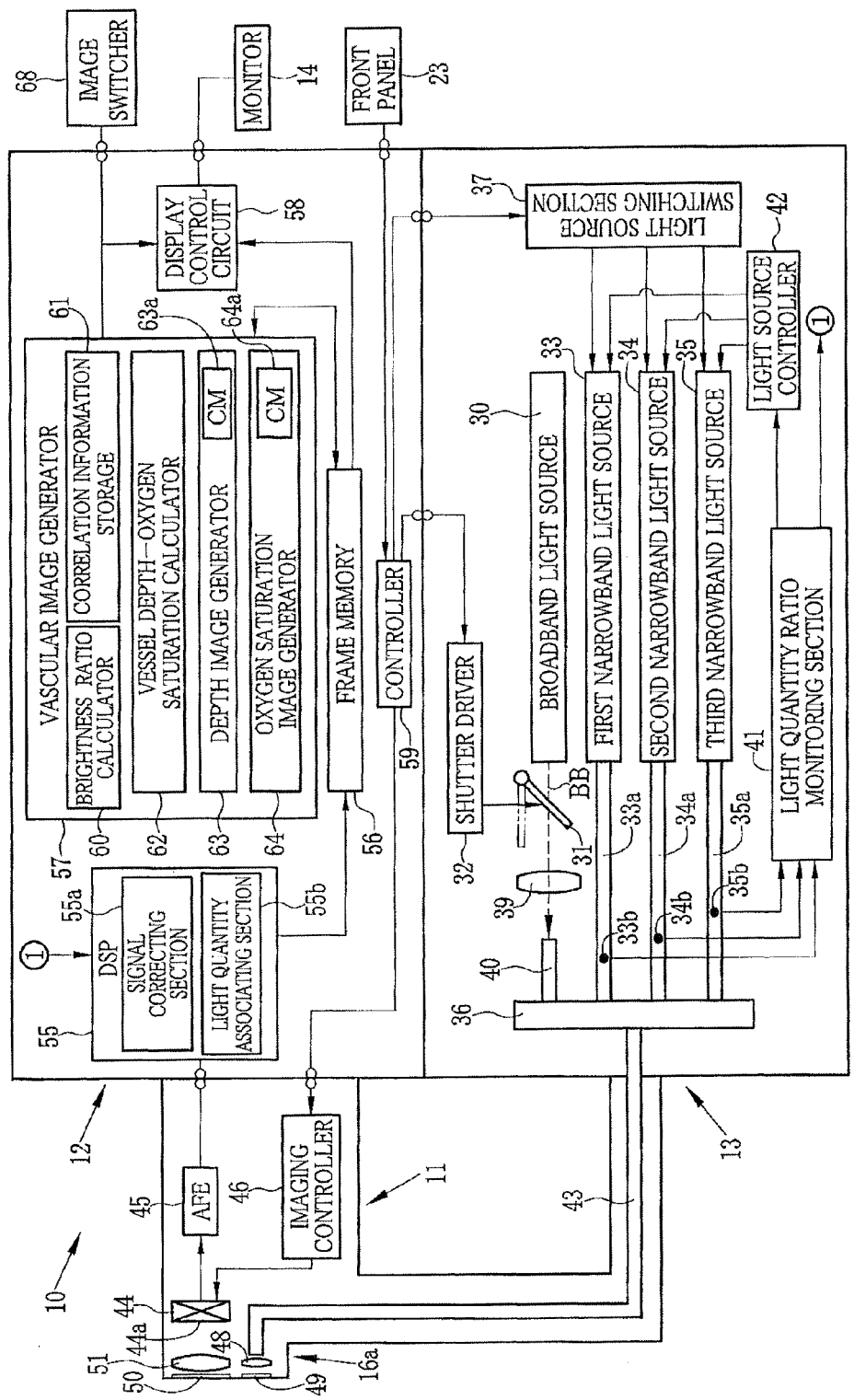
FIG. 2 is a block diagram of an electric configuration of the electronic endoscope system according to the first embodiment.

As shown in FIG. 2, the light source apparatus 13 is provided with a broadband light source 30, a shutter 31, a shutter driver 32, first to third narrowband light sources 33, a coupler 36, and a light source switching section 37. The light source apparatus 13 further includes a light quantity ratio monitoring section 41 and a light source controller 42. The light quantity ratio monitoring section 41 monitors a light quantity ratio among the first to third narrowband light sources 33. The light source controller 42 controls the first to third narrowband light sources 33.

The broadband light source 30 is a xenon lamp, a white LED, a microwhite light source, or the like. The broadband light source 30 emits broadband light BB in a wavelength range from red to blue (approximately from 470 nm to 700 nm). The broadband light source 30 is kept turned on while the electronic endoscope 11 is in use. The broadband light BB emitted from the broadband light source 30 is collected by a condenser lens 39 into a broadband optical fiber 40.

The shutter 31 is provided between the broadband light source 30 and the condenser lens 39. The shutter 31 is movable between an insert position and a retract position. In the insert position, the shutter 31 is inserted in an optical path of the broadband light BB to block the broadband light BB. In the retract position, the shutter 31 retracts from the insert position to allow the broadband light BB to enter the condenser lens 39. The shutter driver 32 is connected to a controller 59 in the processing apparatus 12, and controls the shutter 31 based on an instruction from the controller 59.

The first to third narrowband light sources 33 to 35 emit first to third narrowband lights N1 to N3 as the first to third illumination lights, respectively. Each of the narrowband lights N1 to N3 has a wavelength range within a narrowband. Each of the first to third narrowband light sources 33 to 35 is composed of a semiconductor light source, for example, a laser diode or an LED. The first narrowband light source 33 generates the first narrowband light N1 in a wavelength range of 440±10 nm, preferably 445 nm. The second narrowband light source 34 generates the second narrowband light N2 in a wavelength range of 470±10 nm, preferably 473 nm. The third narrowband light source 35 generates the third narrowband light N3 in a wavelength range of 400±10 nm, preferably 405 nm. The first to third narrowband, lights N1 to N3 are narrowband lights (hereinafter referred to as the blue narrowband lights) in the blue region. Each of the first and second narrowband lights N1 and N2 varies in absorbance in accordance with oxygen saturation of hemoglobin in a blood vessel, which will be described later. The third narrowband light N3 is used as reference light to obtain a reference signal. The reference signal is used for comparison with an imaging signal corresponding to the first narrowband light N1 and an imaging signal corresponding to the second narrowband light N2.

Each of the first to third narrowband light sources 33 to 35 is connected to the light source controller 42. The light source controller 42 controls the first to third narrowband light sources 33 to 35 to adjust the light quantity of each of the first to third narrowband lights N1 to N3 within a predetermined range. The first to third narrowband light sources 33 to 35 are connected to first to third narrowband optical fibers 33a to 35a, respectively. The first narrowband light N1 from the first narrowband light source 33 is incident on the first narrowband optical fiber 33a. The second narrowband light N2 from the second narrowband light source 34 is incident on the second narrowband optical fiber 34a. The third narrowband light N3 from the third narrowband light source 35 is incident on the third narrowband optical fiber 35a.

The coupler 36 connects the broadband optical fiber 40 and the first to third narrowband optical fibers 33a to 35a to the light guide 43 of the electronic endoscope 11. The coupler 36 allows the broadband light BB to enter the light guide 43 through the broadband optical fiber 40. The coupler 36 allows the first to third narrowband lights N1 to N3 to enter the light guide 43 through the respective first to third narrowband optical fibers 33a to 35a.

The light source switching section 37 is connected to the controller 59 in the processing apparatus. Based on an instruction from the controller 59, the light source switching section 37 turns on or off each of the first to third narrowband light sources 33 to 35. In the first embodiment, when the electronic endoscope system 10 is set to a normal mode, the broadband light BB is applied to the patient's body cavity to capture a normal light image while the first to third narrowband light sources 33 to 35 are turned off. On the other hand, when the electronic endoscope system 10 is set to a special mode, the application of the broadband light BB to the body cavity is stopped, and each of the first to third narrowband light sources 33 to 35 is sequentially turned on to capture a special light image.

To be more specific, firstly, the light source switching section 37 turns on the first narrowband light source 33. An image of an objective tissue is captured while the first narrowband light N1 is applied to the body cavity. When the image capture is completed, the controller 59 issues an instruction to switch the light source. Thereby, the light source switching section 37 turns off first narrowband light source 33, and then turns on the second narrowband light source 34. When image capture with the application of the second narrowband light N2 to the body cavity is completed, the light source switching section 37 turns off the second narrowband light source 34, and then turns on the third narrowband light source 35. When image capture with the application of the third narrowband light N3 to the body cavity is completed, the light source switching section 37 turns off the third narrowband light source 35.

The light quantity monitoring section 41 monitors a light quantity ratio among the first to third narrowband lights N1 to N3. To monitor the light quantity ratio, the light quantity detectors 33b to 35b are attached to the first to third narrowband optical fibers 33a to 35a, respectively. The first to third narrowband lights N1 to N3 are guided to the first to third narrowband optical fibers 33a to 35a, respectively. The light quantity detectors 33b to 35b detect the light quantities of the first to third narrowband lights N1 to N3, respectively. The light quantity signal values detected by the light quantity detectors 33b to 35b are sent to the light quantity monitoring section 41 and then to a digital signal processor (hereinafter abbreviated as the DSP) 55 of the processing apparatus 12. The light quantity monitoring section 41 monitors the light quantity ratio among the first to third narrowband lights N1 to N3 based on the light quantity signal values.

In this embodiment, the light quantity monitoring section 41 monitors a first light quantity ratio L1/L3 and a second light quantity ratio L2/L3. The first light quantity ratio L1/L3 is a ratio between a light quantity L1 of the first narrowband light N1 and a light quantity L3 of the third narrowband light N3. The second light quantity ratio L2/L3 is a ratio between a light quantity L2 of the second narrowband light N2 and the light quantity L3 of the third narrowband light N3. In the monitoring, a difference value between the first light quantity ratio L1/L3 being monitored and a predetermined first standard light quantity ratio, and a difference value between the second light quantity ratio L2/L3 being monitored and a predetermined second standard light quantity ratio are obtained. The difference values are sent to the light source controller 42.

The light source controller 42 controls the first to third narrowband light sources 33 to 35 based on the difference values from the light quantity monitoring section 41. The light source controller 42 controls the light quantities of the first narrowband light N1 emitted from the first narrowband light source 33, the second narrowband light N2 emitted from the second narrowband light source 34, and the third narrowband light N3 emitted from the third narrowband light source 35 such that the first light quantity ratio L1/L3 stays within the first standard light quantity ratio and the second light quantity ratio L2/L3 stays within the second standard light quantity ratio. Each of the first and second standard light quantity ratios is predetermined before the use of the electronic endoscope, for example, at the time of shipping or regular maintenance of the electronic endoscope system. The first and second standard light quantity ratios are stored in an internal memory such as a ROM or a RAM in the controller 59, for example.

In this embodiment, the first light quantity ratio L1/L3 and the second light quantity ratio L2/L3 are monitored for the following reasons. In this embodiment, a vessel depth and the oxygen saturation are obtained simultaneously based on the comparison (value comparison) between first and second brightness ratios S1/S3 and S2/S3, which will be described later. The first brightness ratio S1/S3 is obtained from images captured with the illumination of the first and third narrowband lights N1 and N3, respectively. The second brightness ratio S2/S3 is obtained from images captured with the illumination of the second third narrowband lights N2 and N3, respectively. The first brightness ratio S1/S3 corresponds to the first light quantity ratio L1/L3. The second brightness ratio S2/S3 corresponds to the second light quantity ratio L2/L3. Accordingly, when the light quantity ratios, namely, the differences in the light quantities among the first to third narrowband light sources 33 to 35 fluctuate, noise caused by the fluctuation contaminates the first brightness ratio S1/S3 and the second brightness ratio S2/S3. As a result, the vessel depth and the oxygen saturation cannot be obtained accurately. To prevent the noise, the first and second light quantity ratios L1/L3 and L2/L3 are controlled to be kept or adjusted to constant values (the first and second standard light quantity values), respectively. Thus, the first and second brightness ratios S1/S3 and S2/S3 are obtained accurately without influence of the noise, and as a result, the vessel depth and the oxygen saturation are determined accurately.

The light quantity ratio among the first to third narrowband lights N1 to N3 is preferably within the order of ±2% relative to a standard light quantity ratio for the following reason. For example, when the oxygen saturation is calculated using three kinds of wavelengths (405 nm, 445 nm, and 473 nm), a change in a light quantity ratio 473 nm/445 nm corresponding to a 20% change in the oxygen saturation is typically a little over 10% according to findings from imaging experiments of animal digestive mucosa and human lip mucosa. To calculate the change with stability and accuracy, the light quantity ratio among the first to third narrowband lights N1 to N3 needs to be controlled within the order of ±2% relative to the standard light quantity in consideration of hypoxic condition or low oxygen level caused by cancer.

The electronic endoscope 11 is provided with a light guide 43, a CCD 44, an AFE (analog front end) 45, and an imaging controller 46. The light guide 43 is, for example, a large core optical fiber or a bundle fiber, and its input end is inserted into the coupler 36 in the light source apparatus 13 and its exit end is directed to an illumination lens 48. The light guide 43 delivers the light emitted from the light source apparatus 13 to the illumination lens 48. The light incident on the illumination lens 48 is applied to the body cavity through an illumination window 49 attached to an end surface of the distal portion 16a. The broadband light BB and the first to third narrow band lights N1 to N3 reflected from the body cavity are incident on an imaging lens 51 through a capture window 50 attached to the end surface of the distal portion 16a.

The light from the condenser lens 51 is incident on an imaging surface 44a of the CCD 44. The CCD photoelectrically converts the incident light into signal charge and accumulates the signal charge, and reads out the accumulated signal charge as an imaging signal. The imaging signal is sent to the AFE 45. The CCD 44 is a color CCD. On the imaging surface 44a, red, green, and blue (R, G, and B) pixels are arranged in matrix. The R pixel is provided with a red filter. The G pixel is provided with a green filter. The B pixel is provided with a blue filter.

Figure 3:
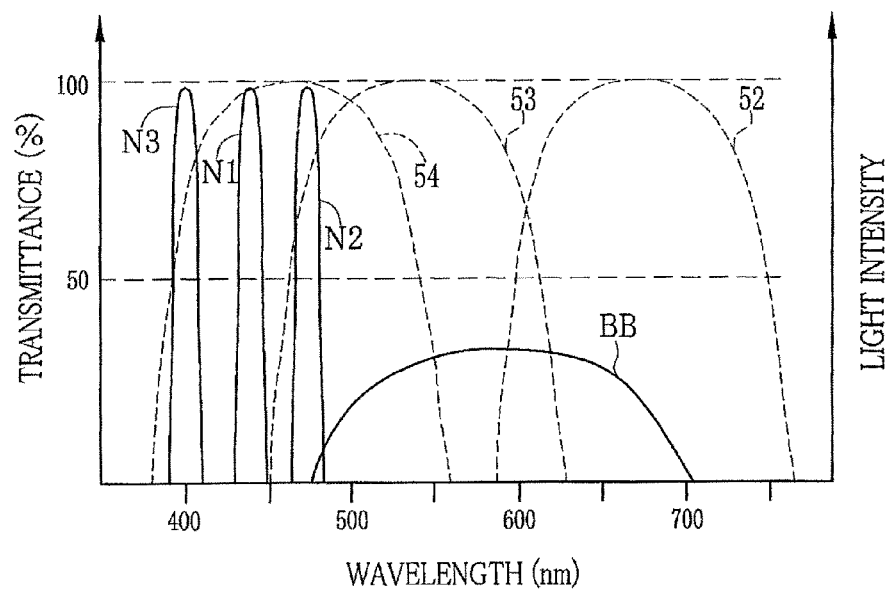
FIG. 3 is a graph showing spectral transmittances of a B pixel, a G pixel, and an R pixel of a color CCD and the broadband light BB and a distribution of light intensities of the first to third narrowband lights N1 to N3.

The red filter (R filter), the green filter (G filter), and the blue filter (B filter) have spectral transmittances 52, 53, and 54, respectively as shown in FIG. 3. Out of the light incident on the imaging lens 51, the broadband light BB is in a wavelength range from approximately 470 nm to 700 nm. The R, G, and B filters pass the light having wavelengths corresponding to the spectral transmittances 52, 53, and 54, respectively. A signal photoelectrically converted in the R pixel is defined as an R imaging signal (red color signal). A signal photoelectrically converted in the G pixel is defined as a G imaging signal (green color signal). A signal photoelectrically converted in the B pixel is defined as a B imaging signal (blue color signal). In the normal mode, when the broadband light BB is incident on the CCD 44, a broadband imaging signal composed of the R, G, and B imaging signals is obtained.

On the other hand, out of the light incident on the imaging lens 51, the first narrowband light N1 is in a wavelength range of 440±10 nm. Accordingly, only the B filter allows to pass the first narrowband light N1. When the first narrowband light N1 is incident on the CCD 44, a first narrowband imaging signal composed of the B imaging signal is obtained. The second narrowband light N2 is in a wavelength range of 470±10 nm. Accordingly, both the B filter and G filter allow to pass the second narrowband light N2. When the second narrowband light N2 is incident on the CCD 44, a second narrowband imaging signal composed of the B and G imaging signals is obtained. The third narrowband light N3 is in a wavelength of 400±10 nm. Accordingly, only the B filter allows to pass the third narrowband light N3. When the third narrowband imaging signal is incident on the CCD 44, a third narrowband imaging signal composed of the B imaging signal is obtained.

The AFE 45 is composed of a correlated double sampling circuit (CDS), an automatic gain control circuit (AGC), and an analog/digital converter (A/D) (all not shown). The CDS performs correlated double sampling to the imaging signal from the CCD 44 to remove noise caused by the CCD 44. Then, the AGC amplifies the imaging signal. Thereafter, the A/D converts the imaging signal into a digital imaging signal having a predetermined number of bits and inputs the digital imaging signal to the processing apparatus 12.

Figure 4A:
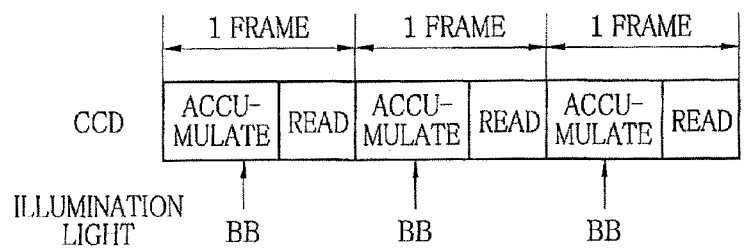
FIG. 4A is an explanatory view describing an imaging operation of a CCD in a normal mode.

The imaging controller 46 is connected to the controller 59 in the processing apparatus 12. The imaging controller 46 sends a drive signal to the CCD 44 upon receiving an instruction from the controller 59. Based on the drive signal, the CCD 44 outputs an imaging signal to the AFE 45 at a predetermined frame rate. In this embodiment, when the electronic endoscope system 10 is set to the normal mode, as shown in FIG. 4A, two steps, the step for photoelectrically converting the broadband light BE into signal charge to accumulate the signal charge and the step for reading the accumulated signal charge as the broadband imaging signal, are performed within a time required for obtaining one frame. The two-step operations are repeated sequentially when the electronic endoscope system 10 is set to the normal mode.

Figure 4B:
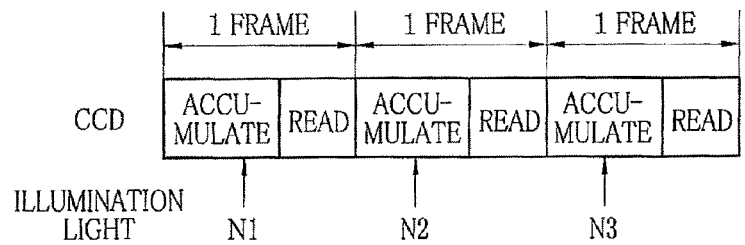
FIG. 4B is an explanatory view describing an imaging operation of the CCD in a special mode.

On the other hand, when the normal mode is switched to the special mode, firstly, as shown in FIG. 4B, two steps, the step for photoelectrically converting the first narrowband light N1 into signal charge to accumulate the signal charge and the step for reading the accumulated signal charge as the first narrowband imaging signal, are performed within the time required for obtaining one frame. When the first narrowband imaging signal is completely read, two steps, the step for photoelectrically converting the second narrowband light N2 into signal charge to accumulate the signal charge and the step for reading the accumulated signal charge as the second narrowband imaging signal are performed within the time required for obtaining one frame. When the readout of the second narrowband imaging signal is completed, two steps, the step for photoelectrically converting the third narrowband light N3 into signal charge to accumulate the signal charge and the step for reading the accumulated signal charge as the third narrowband imaging signal, are performed.

As shown in FIG. 2, the processing apparatus 12 is composed of the DSP 55, a frame memory 56, a vascular image generator 57, and a display control circuit 58. The controller 59 controls each section of the processing apparatus 12. The DSP 55 performs various image processes, such as color separation, color interpolation, white balance adjustment, and gamma correction to the broadband imaging signal outputted from the AFE 45 of the electronic endoscope 11 to generate broadband image data. The frame memory 56 stores the broadband image data generated by the DSP 55. Here, the broadband image data is color image data containing colors of R (red), G (green), and B (blue).

On the other hand, to the first to third narrowband imaging signals outputted from the AFE 45, the DSP 55 performs processes different from those for the broadband imaging signal. First, when the first to third narrowband imaging signals are inputted to the DSP 55. A signal correcting section 55a in the DSP 55 corrects or compensates for fluctuation in the light quantities of the first to third narrowband lights N1 to N3 (or fluctuation of the first light quantity ratio L1/L3 and fluctuation of the second light quantity ratio L2/L3) relative to the first to third narrowband imaging signals. Based on the light quantity signal values of the first to third narrowband lights N1 to N3 detected inside the light source apparatus 13, the signal correcting section 55a corrects all the picture elements in the first to third narrowband images with the use of correction expressions below.

$S1 = c1(L1, L2, L3) \times Sa1$ $S2 = c2(L1, L2, L3) \times Sa2$ $S3 = c3(L1, L2, L3) \times Sa3$ Here, the values Sa1 to Sa3 represent the brightness values (before being corrected) of predetermined picture elements in the first to third narrowband imaging signals, respectively. Correction factor or correction coefficients c1, c2, and c3 are determined by the light quantities L1, L2, and L3 of the first to third narrowband lights N1 to N3. The correction coefficients c1, c2, and c3 are obtained by capturing an image of a reference object while the light quantity ratios of the illumination lights are varied and determining a relationship between the light quantity ratio and the imaging signal ratio between the wavelengths. The reference object has a known reflection spectrum (for example, the reflectance is constant regardless of the wavelengths).

Thereafter, various processes such as the color separation, the color interpolation, the white balance adjustment, and the gamma correction are performed to the first to third narrowband imaging signals to generate first to third narrowband image data. Then, a light quantity associating section 55b in the DSP 55 associates the first to third narrowband image data with the light quantities L1, L2, and L3 of the first to third narrowband lights, respectively. Thereby, the first light quantity ratio L1/L3 and the second light quantity ratio L2/L3 are calculated. The first to third narrowband image data associated to the first to third narrowband lights L1 to L3, respectively, are stored sequentially in the frame memory 56. By storing the light quantity values L1 to L3 obtained through the monitoring in association with the first to third narrowband image data, respectively, the light quantity values L1, L2, and L3 may be used in various analyses other than the above-described corrections. Alternatively or in addition, the light quantity associating section 55b may associate a set of the first to third narrowband image data to a set of the first and second light quantity ratios obtained from the light quantities L1 to L3.

The vascular image generator 57 is provided with a brightness ratio calculator 60, a correlation information storage 61, a vessel depth-oxygen saturation calculator 62, a depth image generator 63, and an oxygen saturation image generator 64. The brightness ratio calculator 60 identifies a vascular region including a blood vessel from the first to third narrowband image data stored in the frame memory 56. The brightness ratio calculator 60 calculates the first brightness ratio S1/S3 between the first and the third narrowband image data relative to the pixels located in the same positions in the blood region and the second brightness ratio S2/S3 between the first and the third narrowband image data relative to the pixels located in the same positions in the blood region. Here, S1 represents the brightness value of a picture element in the vascular region in the first narrowband image data. S2 represents the brightness of a picture element, located in the same position as that of the picture element of the first narrowband image data, in the second narrowband image data. S3 represents the brightness of a picture element, located in the same position as that of the picture element of the first narrowband image data, in the third narrowband image data. The brightness value S3 represents a brightness level of the objective tissue to be observed. The brightness value S3 is a reference signal that standardize the brightness values S1 and S2 and used for comparison with the brightness values S1 and S2.

The vascular region may be determined using a difference between a brightness value of a blood vessel or a portion having the blood vessel and a brightness value of a region other than the blood vessel, for example. In this embodiment, the first and second brightness ratios S1/S3 and S2/S3 are obtained only from the picture elements in the vascular region. Alternatively, the first and second brightness ratios S1/S3 and S2/S3 may be obtained from every picture element including that outside the vascular region in each of the first to third narrowband image data.

Figure 5:
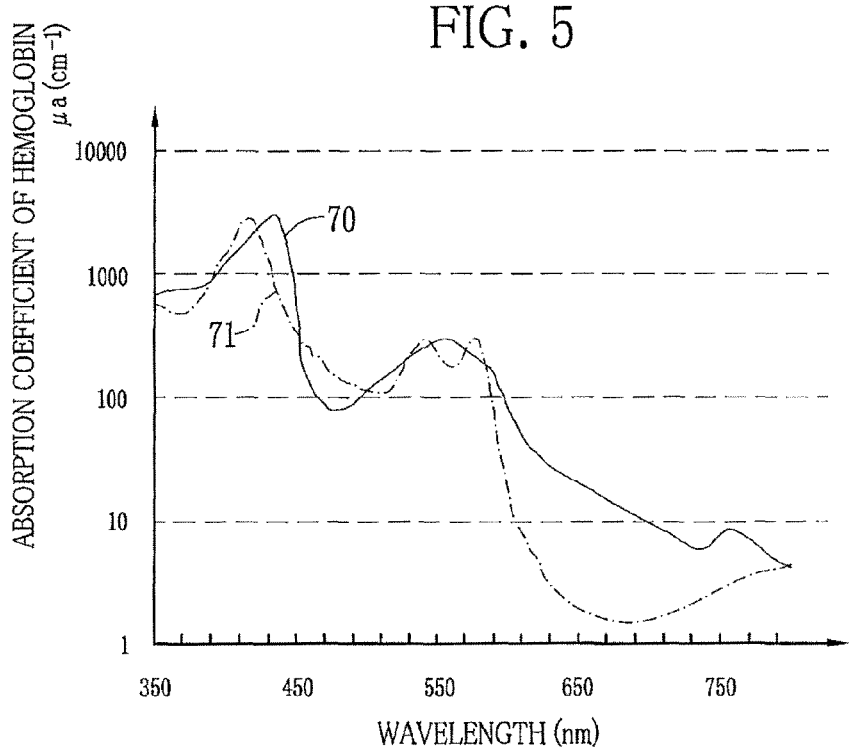
FIG. 5 is a graph of a hemoglobin absorption coefficient.

The correlation information storage 61 stores the first brightness ratio S1/S3 and the second brightness ratio S2/S3, and correlation between the oxygen saturation of hemoglobin in a blood vessel and the depth of the blood vessel. Here, the correlation is based on absorption spectrum of hemoglobin in blood as shown in FIG. 5. The correlation is obtained by analyzing a plurality of the first to third narrowband image data accumulated through past diagnoses and the like. As shown in FIG. 5, an absorption coefficient μa of hemoglobin in the blood vessel changes due to a wavelength of light applied thereto. The absorption coefficient pa represents absorbance that is a quantity of light absorbed by hemoglobin in the blood vessel, and is a coefficient in an expression $I_0\exp(-\mu a \times x)$. The expression $I_0\exp(-\mu a \times x)$ represents attenuation of the light applied to the hemoglobin. The $I_0$ denotes light brightness applied from the light source apparatus to an objective tissue. The x (cm) denotes a depth of the blood vessel.

Absorbance of deoxyhemoglobin 70 is different from that of oxyhemoglobin 71. The deoxyhemoglobin 70 is the form of hemoglobin without the bound oxygen. The oxyhemoglobin 71 is the form of hemoglobin bound with the oxygen. As shown in FIG. 5, the absorbance of the deoxyhemoglobin 70 is different from that of the oxyhemoglobin 71 except for isosbestic points (shown by intersections of the homoglobins 70 and 71) where the absorbance (the absorption coefficient μa) of the deoxyhemoglobin 70 is equal to that of the oxyhemoglobin 71. When a blood vessel has regions with different absorbances, the brightness value varies even if two lights with the same brightness and the same wavelength are applied to the same blood vessel. Furthermore, when two lights with the same light quantities but different wavelengths are applied to the blood vessel, the absorption coefficient pa varies according to the wavelength. As a result, the brightness value varies. Moreover, in FIG. 5, a difference in absorbance between the hemoglobins 70 and 71 varies with the wavelength as apparent from the comparison of a difference in absorbance between the hemoglobins 70 and 71 near 550 nm wavelength and that near 445 nm wavelength (see FIG. 5).

According to the absorption properties of hemoglobin described above, the absorbance varies with the wavelength even if the oxygen saturation is unchanged, and a penetration depth in the mucosa varies with the wavelength. Accordingly, the oxygen saturation information and the vessel depth information are obtained simultaneously with the use of the two lights like the first and second narrowband lights N1 and N2, by comparing the brightness values therebetween. The two lights are different in wavelength ranges. Each of the two lights absorbs the hemoglobin and the hemoglobin 71 differently. The difference in absorption of the hemoglobins 70 and 71 differ between the two lights.

As described in a conventional method disclosed in the Japanese Patent No. 2648494, the light in a wavelength range in which the hemoglobins 70 and 71 are absorbed differently has been used to measure the oxygen saturation from the brightness value thereof. However, the measured value obtained from the brightness value of one light is susceptible to the influence caused by the vessel depth. As a result, a measured value is not accurate. According to the method of the present invention using the two lights, the first and second narrowband lights N1 and N2 in different wavelength ranges, the blood vessel information is obtained in addition to the oxygen saturation information. The influence caused by the vessel depth is removed from the oxygen saturation and thus the accurate oxygen saturation is obtained.

In this embodiment, the narrowband lights in the blue region are used as the first and second narrowband lights N1 and N2. This is because observation of surface blood vessels are often more important than that of the medium-depth (middle) blood vessels in diagnosis of lesion, for example, to determine whether a tumor is benign or malignant. Accordingly, a method that allows detailed observation of the surface blood vessels is required. To meet the requirement, in this embodiment, the lights in the blue region with the shallow penetration depth and suitable for obtaining the information of the surface blood vessels are used.

A reason for using the narrowband lights is as follows. As apparent from the absorption spectrum shown in FIG. 5, a change in the absorbance is abrupt in the blue region compared to those in green and red regions. In the blue region, when a wavelength is slightly shifted, the absorbance changes by a large amount. The intervals between the isosbestic points where the absorbances of the hemoglobins 70 and 71 cross each other (magnitude relation is reversed) are small. When the wavelength range is broad, signals in two regions crossing each other are mixed up so that the brightness values are averaged. As a result, information cannot be obtained with accuracy. To obtain vascular information of surface blood vessels using the lights in the blue region, it is necessary to use wavelength ranges with a width close to an interval between the two isosbestic points. It is more preferable to use narrowband lights with their respective wavelength ranges within the spacing between the two isosbestic points.

As being apparent from the absorption spectrum of the hemoglobin shown in FIG. 5, the absorption coefficient suddenly drops at around the wavelength of 450 nm and up. However, the vascular information is obtained with higher accuracy as the absorption coefficient increases because a difference between the signal value from the vascular region and that from the region other than the vascular region increases. For this reason, in this embodiment, the light in the wavelength range with the center wavelength at or below 450 nm is used as the first narrowband light N1. In addition to the first narrowband light N1, the light with the center wavelength at or below 450 nm may be used as the second narrowband light N2.

The surface blood vessels are thinner than the medium-depth blood vessels, so a light source with a large light quantity is suitable for the observation of the surface blood vessels. Accordingly, a semiconductor light source that allows application of the narrowband light with a high light quantity is used in this embodiment. In this embodiment, the third narrowband light N3, being the reference light, is the light in a wavelength range of $400\pm10$ nm with a center wavelength of 405 nm, that is, an isosbestic point where the absorbances of the hemoglobins 70 and 71 are equal.

Figure 6:
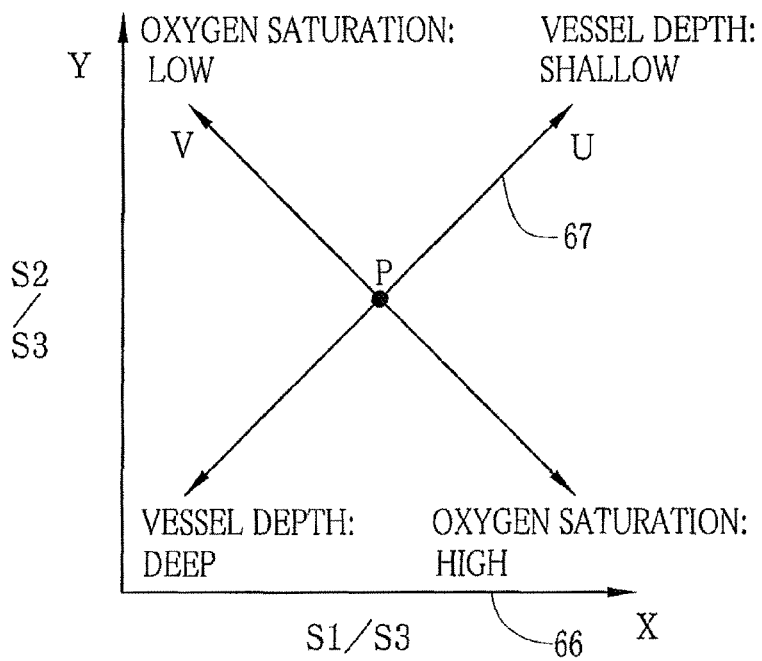
FIG. 6 is a graph showing a correlation between a first brightness ratio S1/S3, a second brightness ratio S2/S3, a vessel depth, and oxygen saturation.

As shown in FIG. 6, the correlation information storage 61 stores the correlation between the brightness ratio and the vessel depth by associating coordinates in a brightness coordinate system 66 with coordinates in a vascular information coordinate system 67. The brightness coordinate system 66 represents the first and second brightness ratios S1/S3 and S2/S3. The vascular information coordinate system 67 represents the oxygen saturation and the vessel depth. The brightness coordinate system 66 is an XY coordinate system. An X axis indicates the first brightness ratio S1/S3. An Y axis indicates the second brightness ratio S2/S3. The vascular information coordinate system 67 is a UV coordinate system provided in the brightness coordinate system 66. A U axis indicates the vessel depth. A V axis indicates the oxygen saturation. The U axis has a positive slope because the vessel depth has positive correlation with the brightness coordinate system 66. The blood vessel becomes shallower as the U axis becomes higher on the right side thereof. On the contrary, the blood vessel becomes deeper as the U axis becomes lower on the left side thereof. On the other hand, the V axis has a negative slope because the oxygen saturation has negative correlation with the brightness coordinate system 66. The oxygen saturation decreases as the V axis becomes higher on the left side thereof. The oxygen saturation increases as the V axis becomes lower on the right side thereof.

In the vascular information coordinate system 67, the U axis and the V axis intersect at right angles at a point of intersection P. This is because the absorbance in the wavelength range of the first narrowband light N1 and that in the wavelength range of the second narrowband light N2 cross each other (magnitude relation is reversed) in the hemoglobin absorption spectrum. Namely, as shown in FIG. 5, in the wavelength range $440\pm10$ nm of the first narrowband light N1, the absorption coefficient of the deoxyhemoglobin 70 is larger than that of the oxyhemoglobin 70. On the other hand, in the wavelength range $470\pm10$ nm of the second narrowband light N2, the absorption coefficient of the oxyhemoglobin 70 is larger than that of the deoxyhemoglobin 70.

The vessel depth-oxygen saturation calculator 62 determines the oxygen saturation and the vessel depth corresponding to the first and second brightness ratios S1/S3 and S2/S3, calculated in the brightness ratio calculator 60, based on the correlation stored in the correlation information storage 61. Out of the first and second brightness ratios S1/S3 and S2/S3, a first brightness ratio in a predetermined picture element in the vascular region is defined as S1*/S3* and a second brightness ratio in the predetermined picture element is defined as S2*/S3*.

Figure 7A:
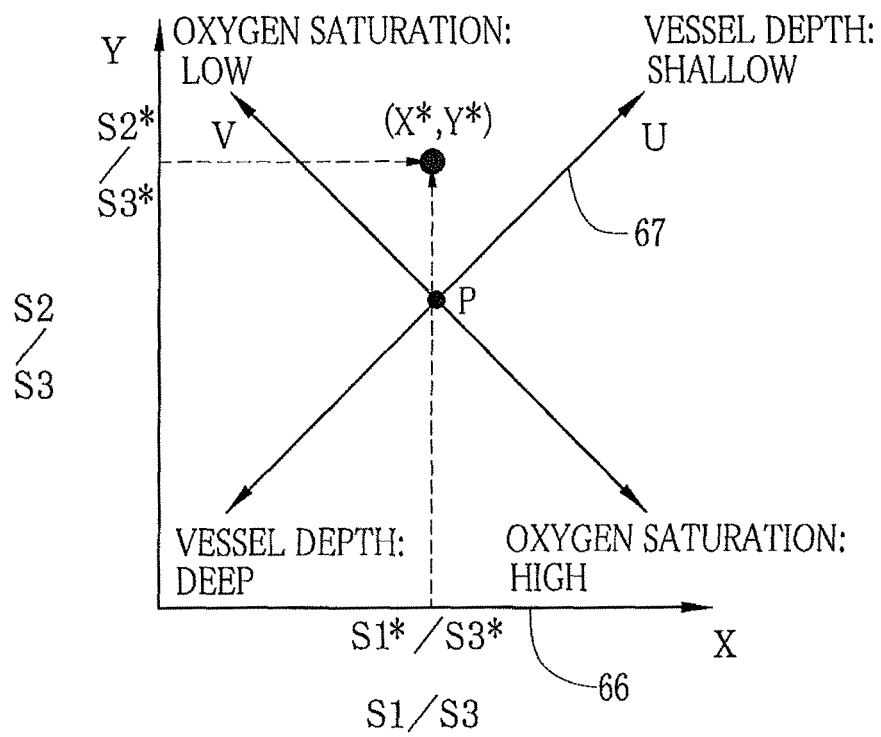
FIG. 7A is an explanatory view of a method for determining coordinates (X*, Y*) in a brightness coordinate system from first and second brightness ratios S1*/S3*, S2*/S3*.
Figure 7B:
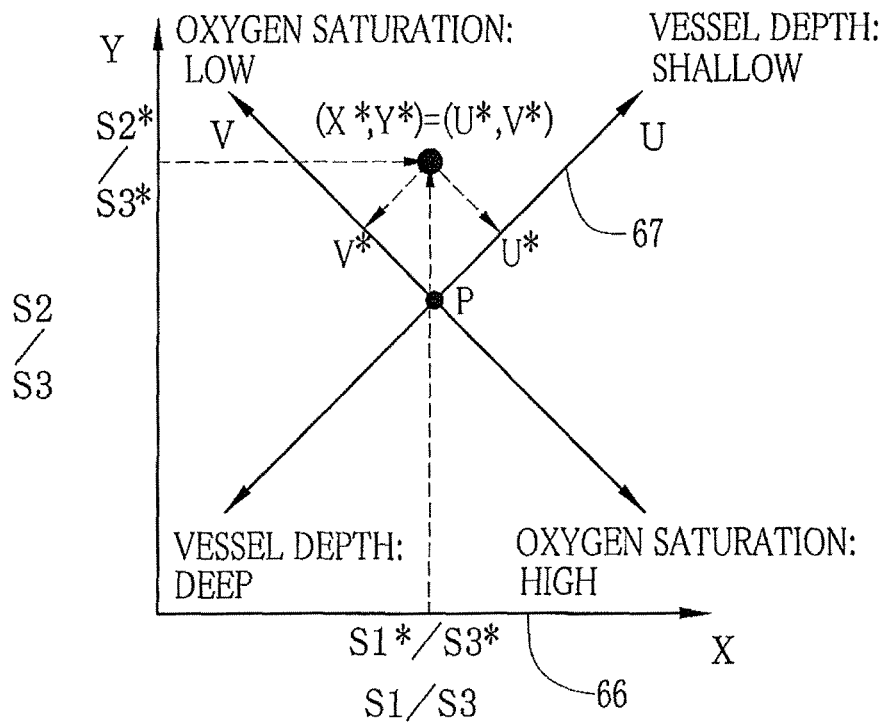
FIG. 7B is an explanatory view of a method for determining coordinates (U*, V*) in a vascular information coordinate system corresponding to the coordinates (X*, Y*)

As shown in FIG. 7A, the vessel depth-oxygen saturation calculator 62 determines the coordinates (X*, Y*) corresponding to the first and second brightness ratios S1*/S3* and S2*/S3* in the brightness coordinate system 66. Then, as shown in FIG. 7B, the coordinates (U*, V*) corresponding to the coordinates (X*, Y*) are determined in the vascular information coordinate system 67. Thus, the vessel depth information U* and the oxygen saturation information V are determined.

In this embodiment, the first and second narrowband lights are in the wavelength ranges ($440\pm10$ nm and $470\pm10$ nm), respectively, in each of which absorbances of the hemoglobins 70 and 71 cross each other (magnitude relation is reversed). Alternatively, other wavelength regions in which the absorbances of the hemoglobins 70 and 71 do not cross with each other may be used. However, the U axis and the V axis do not intersect at a right angle in a 2-dimensional space. In this case, a relationship between the U axis and the V axis may be defined in a 3-dimensional space, for example. Thereby, the coordinates (U*, V*) in the vascular information coordinate system 67 are determined from the coordinates (X*, Y*) determined in the brightness coordinate system 66. Naturally, it is easier to create data necessary for calculation, for example, table data for defining the relationship between the vessel depth and the oxygen saturation, when the U axis and the V axis intersect at a right angle than when they do not. Thus, it is preferable to use two wavelength ranges in which the absorbances of the hemoglobin 70 and 71 cross with each other for the first and second narrowband lights N1 and N2, respectively.

The depth image generator 63 is provided with a color map (hereinafter may be abbreviated as the CM) 63a in which colors or color information is assigned according to the vessel depth. For example, blue is assigned to the surface blood vessels. Green is assigned to the middle blood vessels. Red is assigned to the deep blood vessels. Thus, the color map 63a is color-coded to distinguish between vessel depths clearly. Here, the vessel depth refers to a depth within the penetration depths of the first and second narrowband lights N1 and N2. Because the first and second narrowband lights N1 and N2 are in the blue region, the penetration depths from the surface of the objective tissue are shorter than that of the light in the red region with a longer wavelength than the first and second narrowband lights N1 and N2. Accordingly, the first and second narrowband lights N1 and N2 allow distinguishing between the vessel depths mainly in the surface region. Using the color map 63a, the depth image generator 63 identifies the color or color information corresponding to the vessel depth information U* calculated in the vessel depth-oxygen saturation calculator 62.

After identifying the colors or color information for every picture element in the vascular region, the depth image generator 63 reads the broadband image data from the frame memory 56 and reflects the color information to the broadband image data. Thereby, depth image data having vessel depth information is generated. The depth image data is stored in the frame memory 56. Alternatively, the color information may be reflected to one or a composite of the first to third narrowband image data.

The oxygen saturation image generator 64 is provided with a color map (hereinafter may be abbreviated as the CM) 64a in which colors are assigned according to the degree of the oxygen saturation. For example, cyan is assigned to a region with low oxygen saturation. Magenta is assigned to a region with middle oxygen saturation. Yellow is applied to a region with high oxygen saturation. Thus, the color map 64a is color-coded to distinguish between the degrees of the oxygen saturation clearly. Similar to the depth image generator 63, the oxygen saturation image generator 64 identifies the colors or color information corresponding to the oxygen saturation information V* calculated in the vessel depth-oxygen saturation calculator 62. The color information is reflected to the broadband image data to generate the oxygen saturation image data. As with the depth image data, the oxygen saturation image data is stored in the frame memory 56. Alternatively, the color information may be reflected to one or a composite of the first to third narrowband image data.

Figure 8:
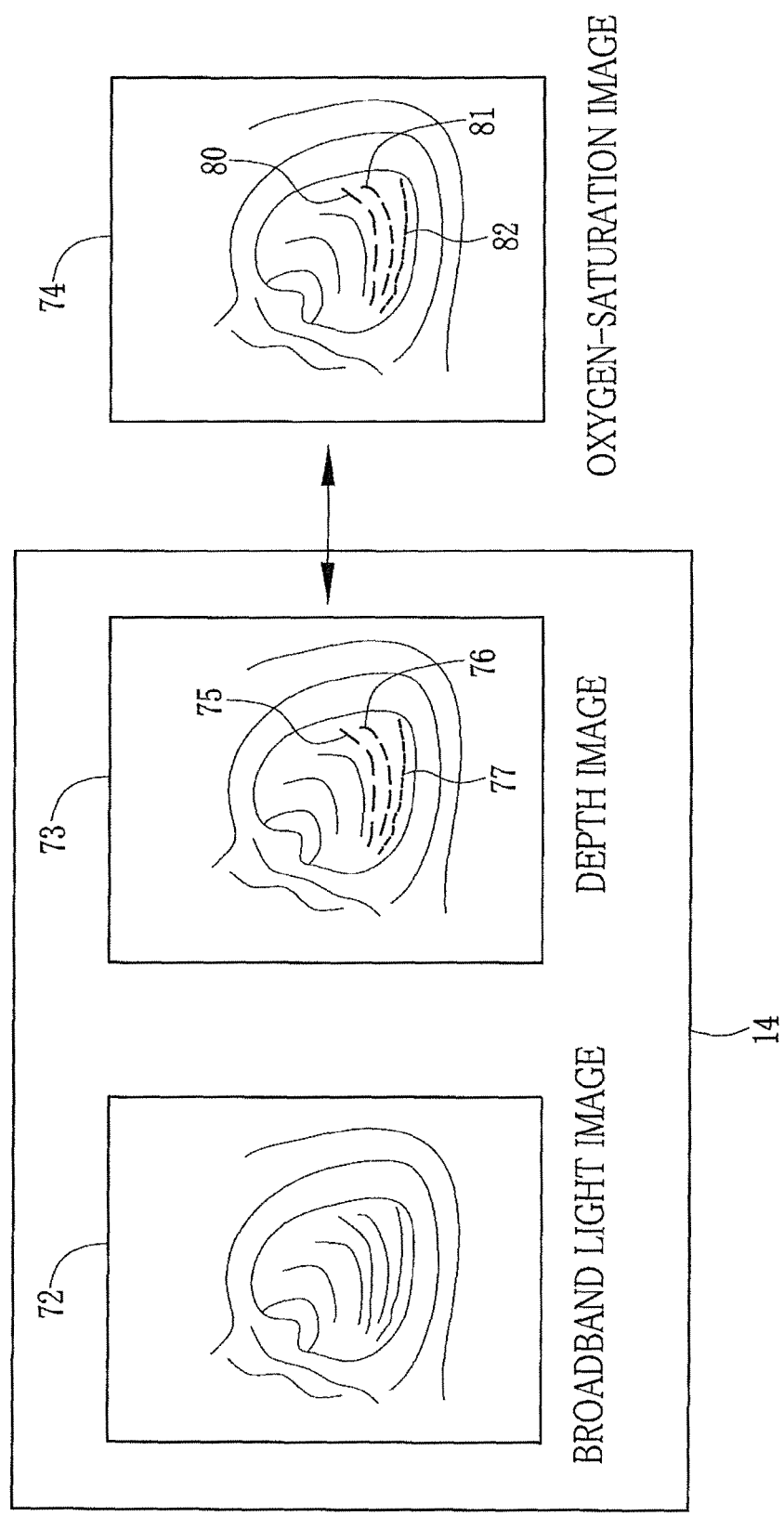
FIG. 8 shows a monitor on which one of the depth image and the oxygen saturation image is displayed.

The display control circuit 58 reads one or more images from the frame memory 56, and displays the one or more images on the monitor 14. The images may be displayed in various patterns. For example, as shown in FIG. 8, a broadband image 72 is displayed on one of the sides of the monitor 14. On the other side of the monitor, a depth image 73 or an oxygen saturation image 74 selected using an image switcher 68 (see FIG. 2) is displayed. In the depth image 73 in FIG. 8, a vascular image 75 is depicted in blue representing the surface blood vessel. A vascular image 76 is depicted in green representing the middle blood vessels. A vascular image 77 is depicted in red representing the deep blood vessel. In the oxygen saturation image 74, a vascular image 80 is depicted by cyan representing low oxygen saturation, and a vascular image 81 is depicted by magenta representing middle oxygen saturation, and a vascular image 82 is depicted by yellow representing high oxygen saturation.

Figure 9:
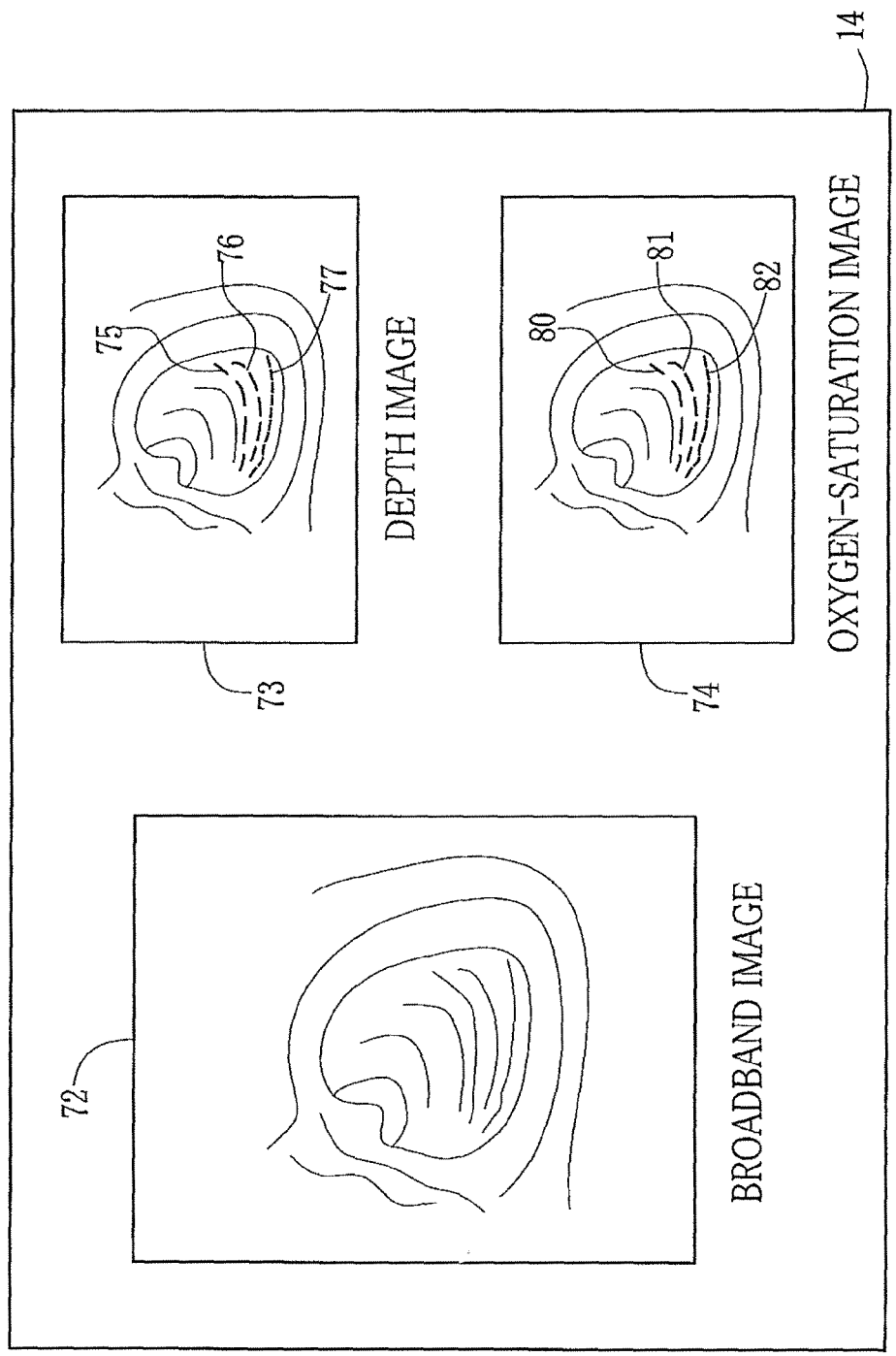
FIG. 9 shows the monitor on which both the depth image and the oxygen saturation image are displayed.
Figure 10:
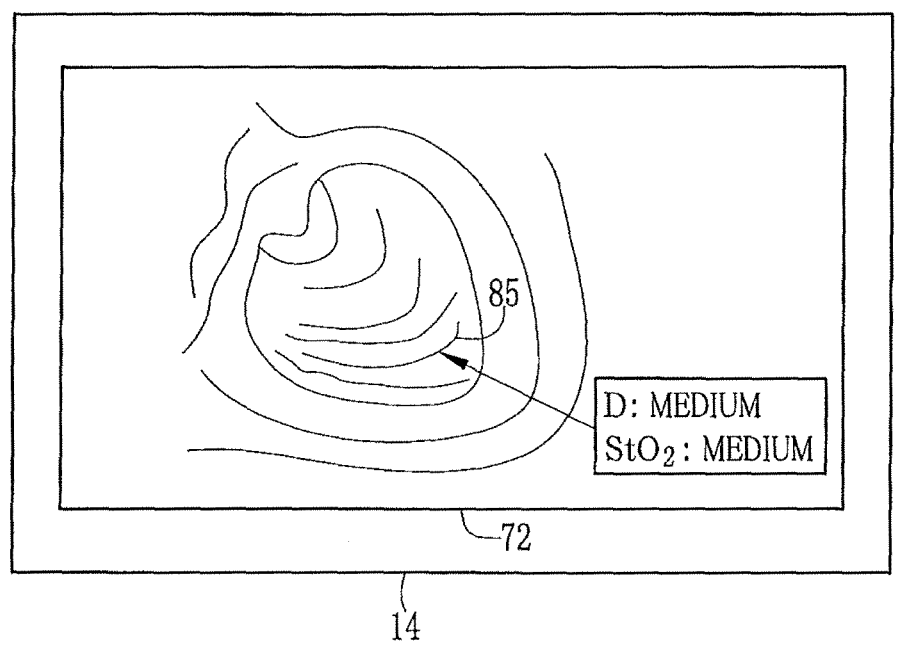
FIG. 10 is the monitor on which the vessel depth information and the oxygen saturation information are simultaneously displayed as the text information.

As shown in FIG. 9, the depth image 73 and the oxygen saturation image 74 may be displayed on the same screen simultaneously. Alternatively, as shown in FIG. 10, the depth image 73 and the oxygen saturation image 74 may not be displayed. In this case, a vascular image 85 of the broadband image 72 may be designated and displayed. The depth (D) and the oxygen saturation ($StO_2$: Saturated Oxygen) of a blood vessel of the vascular image 85 may be displayed as text information.

Figure 11:
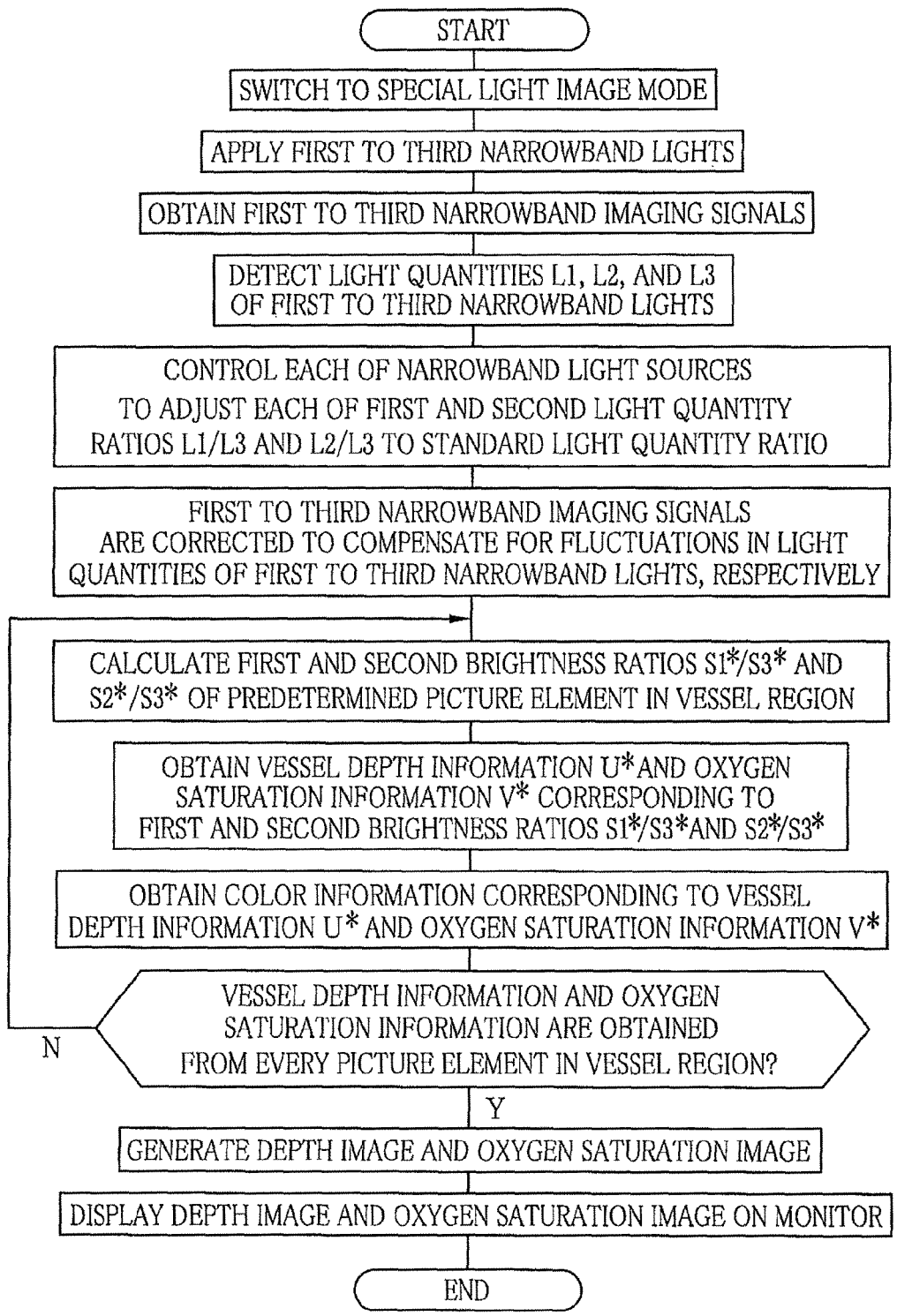
FIG. 11 is a flowchart showing steps for calculating vessel depth-oxygen saturation information and steps for generating a depth image and an oxygen saturation image based on the information calculated.

Next, with reference to a flowchart shown in FIG. 11, steps for calculating vessel depth-oxygen saturation information and steps for generating the depth image and the oxygen saturation image are described. To each of the depth image and the oxygen saturation image, the vessel depth-oxygen saturation information is reflected. First, the normal mode is switched to the special mode by operating the console 23. Thereby, the broadband image data obtained at the time of the switching to the special mode is stored as the image data in the frame memory 56. The image data stored is used for generating the depth image or the oxygen saturation image. The broadband image data obtained in the normal mode (just before the normal mode is switched to the special mode) may be used for generating the depth image and the like.

When the controller 59 sends an application stop signal to the shutter driver 32, the shutter driver 32 moves the shutter 31 from the retract position to the insert position. Thereby, the application of the broadband light BB to the body cavity is stopped. When the application of the broadband light BB is stopped, the controller 59 sends an instruction to start the application of the narrowband light to the light source switching section 37.

Upon receiving the instruction to start the application of the narrowband light, the light source switching section 37 turns on the first narrowband light source 33, and applies the first narrowband light N1 to the body cavity. When the first narrowband light N1 is applied to the body cavity, the controller 59 sends an instruction to capture an image to the imaging controller 46. Thereby, an image is captured while the first narrowband light N1 is applied. Thus, the first narrowband imaging signal is obtained. Similarly, the second narrowband imaging signal is obtained by capturing an image while the second narrowband light N2 is applied, and the third narrowband imaging signal is obtained by capturing an image while the third narrowband light N2 is applied.

When the first narrowband light N1 is applied to the body cavity, the light quantity detector 33b detects the light quantity L1. When the second narrowband light N2 is applied to the body cavity, the light quantity detector 34b detects the light quantity L2. When the third narrowband light N3 is applied to the body cavity, the light quantity detector 35b detects the light quantity L3. The light quantities L1, L2, and L3 are sent as the light quantity signal values to the light quantity monitoring section 41 and the DSP 55. The light quantity monitoring section 41 calculates the first light quantity ratio L1/L3 and the second light quantity ratio L2/L3 from the light quantities L1, L2, and L3, and then calculates the difference value between the first light quantity ratio L1/L3 and its corresponding standard light quantity ratio and the difference value between the second light quantity ratio L2/L3 and its corresponding standard light quantity ratio. Based on the difference values calculated, the light source controller 42 controls the first to third narrowband light sources. The light source controller 42 controls the light quantities of the first to third narrowband lights N1 to N3 such that the first light quantity ratio L1/L3 and the second light quantity ratio L2/L3 reach their respective standard light quantities.

When an image is captured with the CCD 44 before the adjustment of the light quantities of the first to third narrowband lights N1 to N3, the signal correcting section 55a in the DSP 55 corrects the first to third narrowband imaging signals to compensate for the fluctuations in the light quantities of the first to third narrowband lights N 1 to N3 (or the fluctuations in the first light quantity ratio L1/L3 and the second light quantity ratio L2/L3) based on the light quantity ratios L1, L2, and L3 of their respective first to third narrowband lights N1 to N3 detected within the light source apparatus 13. Thereafter, the DSP 55 produces the first to third narrowband image data from the first to third narrowband imaging signals, respectively. The light quantity associating section 55b associates the first to third narrowband image data with the light quantity ratios L1, L2, and L3. Then, the first to third narrowband image data are stored in the frame memory 56. On the other hand, when an image is captured with the CCD 44 after the adjustment of the light quantities of the first to third narrowband lights N1 to N3, a difference value in the light quantity ratio has already been corrected. Therefore, the signal correcting section 55a in the DSP 55 does not necessarily perform the above described correction.

When the broadband image data and the first to third narrowband image data are stored in the frame memory 56, the brightness ratio calculator 60 identifies a vascular region having a blood vessel from the first to third narrowband image data. The first brightness ratio S1*/S3* between the first narrowband image data and third narrowband image data and the second brightness ratio S2*/S3* between the second and third narrowband image data are calculated relative to the same picture elements in the images of the vascular region.

Next, based on the correlation information stored in the correlation information storage 61, the vessel depth-oxygen saturation calculator 62 identifies coordinates (X*, Y*) of the brightness coordinate system 66 corresponding to the first and second brightness ratios S1*/S3* and S2*/S3*. Further, by identifying the coordinates (U*, V*), of the vascular information coordinate system, corresponding to the coordinates (X*, Y*), the vessel depth information U* and the oxygen saturation information V* are obtained relative to a predetermined picture element in the vascular region.

When the vessel depth information U* and the oxygen saturation information V are obtained, color information corresponding to the vessel depth information U is identified using the CM 63a of the depth image generator 63, and color information corresponding to the oxygen saturation information V* is identified using the CM 64 of the oxygen saturation image generator. The identified color information is stored in the RAM (not shown) in the processing apparatus 12.

Thereafter, the vessel depth information U* and the oxygen saturation information V* are obtained for every picture element in the vascular region by performing the above-described steps. Then, the color information corresponding to the vessel depth information U* and the color information corresponding to the oxygen saturation information V* are identified for every picture element.

Thereafter, the depth image generator 63 reads the broadband image data from the frame memory 56. The color information stored in the RAM is reflected to the broadband image data. Thus, the depth image data is generated. The oxygen saturation image generator 64 generates the oxygen saturation image data in the same manner as the depth image. The depth image data and the oxygen saturation image data are stored in the frame memory 56.

The display control circuit 58 reads the broadband image data, the depth image data, and the oxygen saturation image data from the frame memory 56. Based on the image data, the display control circuit 58 displays the broadband image 72, the depth image 73, and the oxygen saturation image 74 on the monitor 14 as shown in FIGS. 8 and 9. In FIG. 8, the broadband image 72 that is the normal light image and one of the depth image 73 and the oxygen saturation image 74 are displayed side by side on the monitor 14. In FIG. 9, the three images (the broadband image 72, the depth image 73, and the oxygen saturation image 74) are displayed simultaneously on the monitor 14.

As described above, the light quantities of the first to third narrowband lights N1 to N3 are controlled such that the first light quantity ratio L1/L3 and the second light quantity ratio L2/L3 reach their respective standard light quantity ratios. Thereby, The first and second light quantity ratios L1/L3 and L2/L3 are obtained accurately without the influence of noise caused by fluctuations in the light quantities of the first to third narrowband light sources 33 to 35. As a result, the vessel depth and the oxygen saturation are determined with high accuracy. Thus, the vessel depth and the oxygen saturation are determined with stability and unaffected by the unstable light sources.

In this embodiment, the first to third imaging signals are corrected in addition to controlling the light quantities of the first to third narrowband lights N1 to N3 based on the first and second light quantity ratios L1/L3 and L2/L3. Alternatively, one of the light quantity control and the signal correction may be performed.

The first and second light quantity ratios L1/L3 and L2/L3 may take different values. For example, the first light quantity ratio L1/L3 may be "1", and the second light quantity ratio L2/L3 may be "2". Alternatively, the first and second light quantity ratios L1/L3 and L2/L3 may take the same value. For example, both the first and second light quantity ratios L1/L3 and L2/L3 may be "1".

Figure 12:
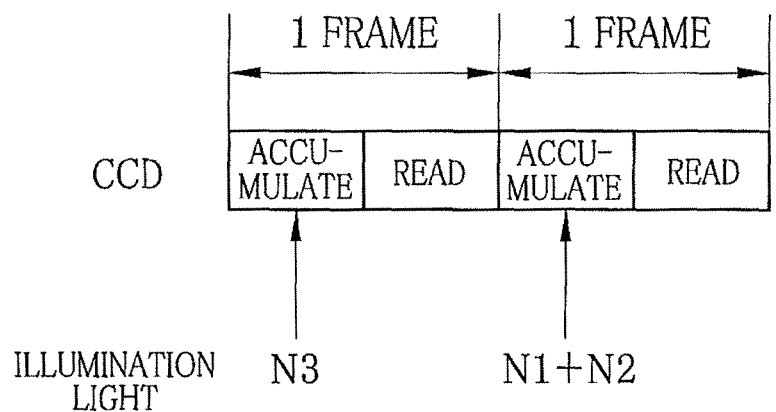
FIG. 12 is an explanatory view of an imaging operation of a CCD according to a second embodiment of the present invention.

A second embodiment of the present invention is different from the first embodiment. In the first embodiment, an imaging signal is obtained with the application of each of the first to third narrowband lights N1 to N3, namely, the total of three frames of imaging signals is captured. In the second embodiment, as shown in FIG. 12, an image is captured with the application of the third narrowband light N3. Then, an image is captured with application of composite narrowband light in which the first narrowband light N1 and the second narrowband light N2 are combined. Thus, a total of two frames of imaging signals are obtained. The first to third narrowband image data is generated from the two frames of imaging signals. Unlike the first embodiment that requires three frames of imaging signals to generate the first to third narrowband image data, the second embodiment requires only two frames of imaging signals. The vessel depth information and the oxygen saturation information are determined using the brightness ratios among first to third narrowband image data relative to the picture elements of the same position. Accordingly, using a small number of frames makes it easy to prevent positional deviation of the picture element caused by motion of the patient and/or the insert section.

In the second embodiment, the electronic endoscope system is the same as or similar to the electronic endoscope system 10 of the first embodiment except for a switching sequence of the first to third narrowband lights 33 to 35 and an imaging signal outputted from the CCD 44. Descriptions of the members similar to the first embodiment are omitted.

In the normal mode, the first to third narrowband light sources 33 to 35 are turned off. When the normal mode is switched to the special mode, the light source switching section 37 turns on the third narrowband light source 35. While the third narrowband light N3 illuminates the body cavity, an image of the objective tissue is captured. When the image capture is completed, the controller 59 instructs to switch the light sources. Here, the third narrowband light source 35 is turned off, and the first and second narrowband light sources 33 and 34 are turned on. While the composite narrowband light of the first and second narrowband lights N1 and N2 illuminates the body cavity, an image of the objective tissue is captured. When the image capture is completed, the first and second narrowband light sources 33 and 34 are turned off.

In the second embodiment, the imaging signal is outputted from the CCD 44 as follows. First, the third narrowband light N3 applied to the body cavity only passes through the B pixel. Accordingly, an imaging signal B1 having only the brightness value S3 corresponding to the third narrowband light N3 is obtained. Then, when the composite narrowband light is applied, the first narrowband light N1 passes through the B pixel while the second narrowband light N2 passes through the B and G pixels. Accordingly, an imaging signal B2 and an imaging signal G2 are obtained. The imaging signal B2 is composed of the brightness value S1 corresponding to the first narrowband light N1 and the brightness value S2 corresponding to the second narrowband light N2. The imaging signal G2 has only the brightness value S2. Thus, the following imaging signals are sent from the CCD 44 to the DSP 55 of the processor apparatus 12.

imaging signal $B1$=brightness value $S3$ imaging signal $B2$=brightness value $S1$+brightness value $S2$ imaging signal $G2$=brightness value $S2$ In the DSP 55, the first to third narrowband image data are generated based on the imaging signal B1, the imaging signal B2, and the imaging signal G2. The imaging signal B1 has only the brightness value S3, so the third narrowband image data is generated from the imaging signal B1. The imaging signal G2 has only the brightness value S2, so the second narrowband image data is generated from the imaging signal G2. On the other hand, the first narrowband image data is generated by calculating B2−(a constant)×G2 to separate the brightness value S2 from the imaging signal B2. The constant is determined from an intensity ratio between the first and second narrowband lights N1 and N2. The first to third narrowband image data generated are stored in the frame memory 56.

Figure 13:
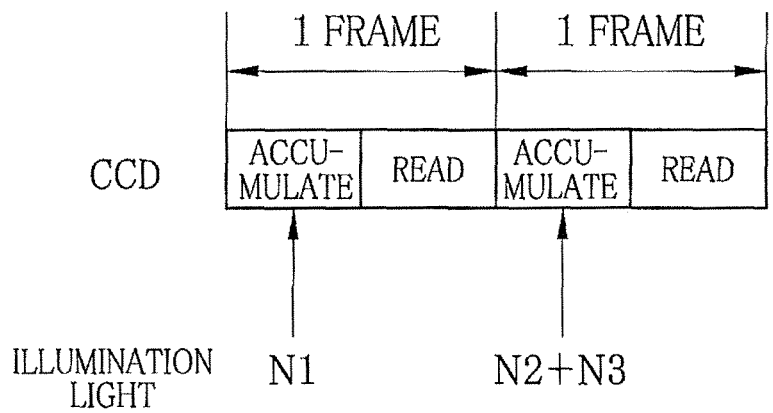
FIG. 13 is an explanatory view of an imaging operation of another CCD according to the second embodiment of the present invention.

Alternatively, in the second embodiment, as shown in FIG. 13, the first narrowband light N1 may be applied first. Then, composite narrowband light of the second narrowband light N2 and the third narrowband light N3 may be applied. In this case, the following imaging signals are obtained.

imaging signal $B1$=brightness value $S1$ corresponding to the first narrowband light $N1$ imaging signal $B2$=brightness value $S2$ corresponding to the second narrowband light $N2$+brightness value $S3$ corresponding to the third narrowband light $N3$ imaging signal $G2$=brightness value $S2$ corresponding to the second narrowband light $N2$ In the DSP 55, the first narrowband image data is generated from the imaging signal B1. The second narrowband image data is generated from the imaging signal G2. On the other hand, the third narrowband image data is generated by calculating B2−(a constant)×G2 to separate the brightness value S2 from the imaging signal B2. The constant is determined from an intensity ratio between the second and third narrowband lights N2 and N3.

Figure 14:
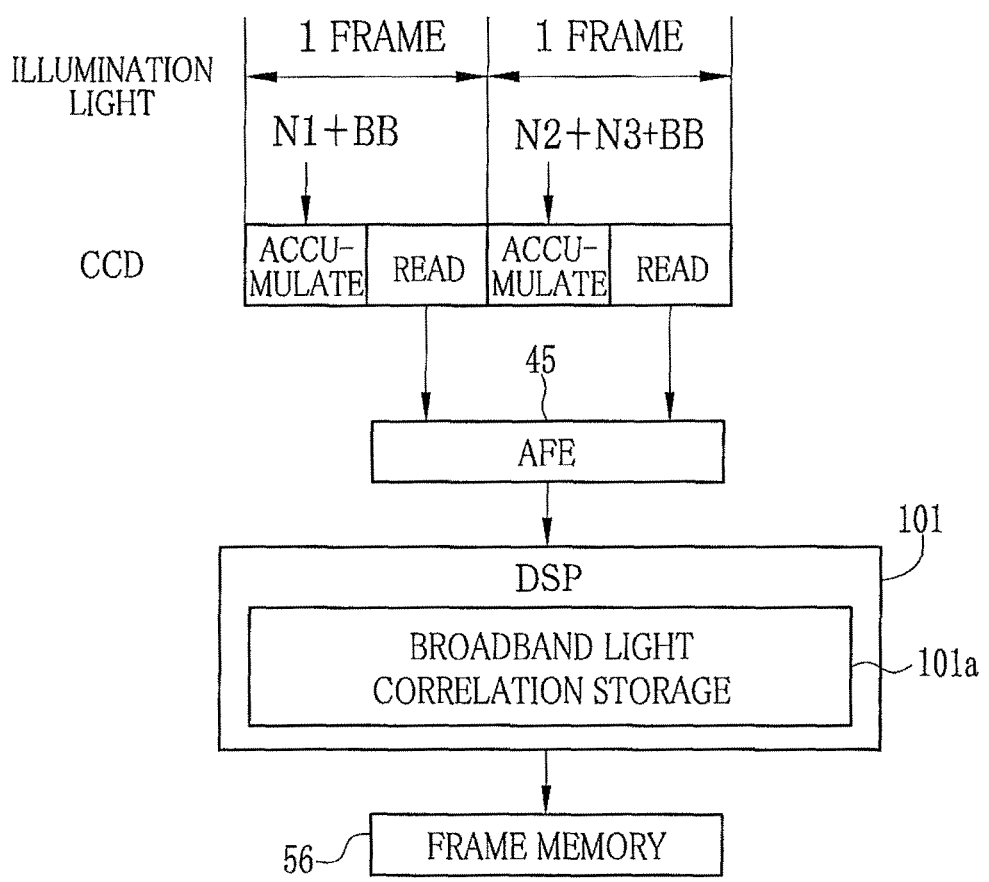
FIG. 14 is an explanatory view of a CCD according to a third embodiment of the present invention.

In the first and second embodiments, the broadband light BB is not applied during the application of the first to third narrowband lights N1 to N3. On the other hand, in a third embodiment of the present invention as shown in FIG. 14, an image is captured while the first narrowband light N1 and the broadband light BB are applied simultaneously. Then, an image is captured while the second narrowband light N2, the third narrowband light N3, and the broadband light BB are applied simultaneously. Thereby, two frames of imaging signals are obtained from the two image captures. The first to third narrowband image data are generated from the two frames of the imaging signals. In the third embodiment, the broadband image data can be generated along with the first to third narrowband image data. When the broadband image and the vessel depth or the oxygen saturation are displayed side by side as shown in FIGS. 8 to 10, display simultaneity is further ensured compared to the first and second embodiments.

The electronic endoscope system of the third embodiment is the same as or similar to the electronic endoscope system 10 of the first embodiment except for a DSP 101 shown in FIG. 14 used instead of the DSP 55 of the first embodiment, actuation of the shutter, a switching sequence of the first to third narrowband light sources 33 to 35, and an imaging signal outputted from the CCD 44. Accordingly, descriptions of the members similar to those of the first embodiment are omitted.

In the third embodiment, the shutter 31 is kept constantly at a retract position, namely, the broadband light source 30 is kept turned on. The broadband light BB is applied to the body cavity constantly during the use of the electronic endoscope 11. The first to third narrowband light sources 33 to 35 are turned off in the normal mode. When the normal mode is switched to the special mode, the light source switching section 37 turns on the first narrowband light source 33. An image of the objective tissue is captured while the first narrowband light N1 and the broadband light BB are applied to the body cavity. When the image capture is completed, the controller 59 instructs to switch the light sources. The first narrowband light source 33 is turned off, and the second and third narrowband light sources 34 and 35 are turned on. Then, an image is captured while the second narrowband light N2, the third narrowband light N3, and the broadband light BE are applied to the body cavity. When the image capture is completed the second and third narrowband light sources 34 and 35 are turned off.

In the third embodiment, the CCD 44 outputs the imaging signal as follows. First, out of the light incident on the imaging surface 44a of the CCD 44, the first narrowband light N1 passes through the B pixel while the broadband light BB passes through both the B pixel and G pixel. Thereby, an imaging signal B1 and an imaging signal G1 are obtained. The imaging signal B1 is composed of the brightness value S1 corresponding to the first narrowband light N1 and the brightness value Broad_B1 corresponding to the broadband light BB. The imaging signal G1 has only the brightness value Broad_G1 corresponding to the broadband light BB.

Next, out of the light incident on the imaging surface 44a of the CCD 44, the second narrowband light N2 and the broadband light BB pass both the B pixel and the G pixel while the third narrowband light N3 passes only the B pixel. Thereby, an imaging signal B2 and an imaging signal G2 are obtained. The imaging signal B2 is composed of the brightness value S2 corresponding to the second narrowband light N2, the brightness value S3 corresponding to the third narrowband light N3, and the brightness value Broad_B2 corresponding to the broadband light BB. The imaging signal G2 is composed of the brightness value S2 corresponding to the second narrowband light N2 and the brightness value Broad_G2 corresponding to the broadband light BB. Thus, the following imaging signals are sent from the CCD 44 to the DSP 101 of the processor apparatus.

imaging signal $B1$=brightness value $S1$+brightness value Broad_$B1$ imaging signal $G1$=brightness value Broad_$G1$ imaging signal $B2$=brightness value $S2$+brightness value $S3$+brightness value Broad_$B2$ imaging signal $G2$=brightness value $S2$+brightness value Broad_$G2$ In the third embodiment, the DSP 101 is provided with a broadband-brightness correlation storage 101a that stores information on correlation among the brightness values Broad_B1, the Broad_G1, the Broad_B2, and the Broad_G2. The correlation information is obtained from the analyses of a plurality of image data accumulated through the past diagnoses. The DSP 101 refers to the correlation information in the broadband-brightness correlation storage 101a to determine the brightness values Broad_B1, the Broad_B2, and the Broad_G2 in correlation with the brightness value Broad_G1. Then, the DSP 101 separates the brightness values Broad_B1, Broad_B2, and Broad_G2 from the imaging signal B1, the imaging signal B2, and the imaging signal G2, respectively.

imaging signal $B1^*$=brightness value $S1$ imaging signal $B2^*$=brightness value $S2$+brightness value $S3$ imaging signal $G2^*$=brightness value $S2$ The DSP 101 obtains the first narrowband image data and second narrowband image data based on the imaging signal $B1^*$ and the imaging signal $G2^*$, respectively. On the other hand, the DSP 101 performs calculation of $B2^*$−(constant)× $G2^*$ to separate the brightness value S2 from the imaging signal $B2^*$ to obtain the third narrowband image data. The constant is determined by an intensity ratio between the second and third narrowband lights. The first to third narrowband image data obtained are stored in the frame memory 56.

In the third embodiment, the brightness values Broad_B1, Broad_G1, Broad_B2, and Broad_G2 are obtained. Accordingly, in the special mode, the broadband image data (the image data of the normal light image), being the color image data is obtained together with the first narrowband image data (the image data of the special light image). In the third embodiment, the first narrowband light N1 and the third narrowband light N3 may be replaced with each other as in the second embodiment (see FIGS. 12 and 13).

In the first to third embodiments, the first light quantity ratio L1/L3 and the second light quantity ratio L2/L3 are monitored constantly in the light source apparatus 13. In a fourth embodiment of the present invention, on the other hand, predetermined processes performed before the use of the electronic endoscope makes the constant monitoring unnecessary when the light quantity ratios do not fluctuate largely in a short time.

Figure 15:
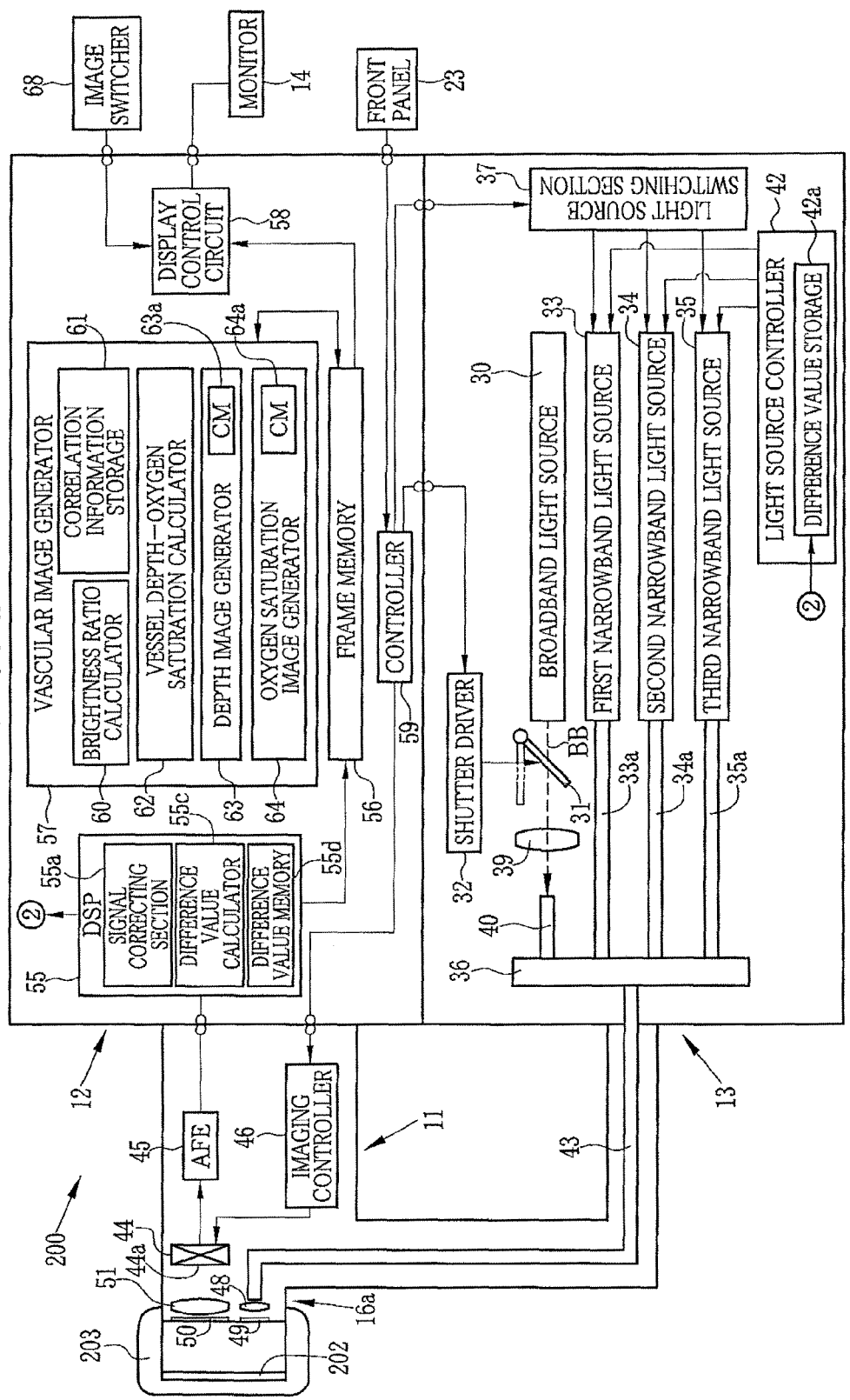
FIG. 15 is a block diagram of an electric configuration of an electronic endoscope system according to a fourth embodiment of the present invention.

In the fourth embodiment, as shown in FIG. 15, in the electronic endoscope system 200, an image of a reference object 202 is captured before the use of the electronic endoscope system 200. The reference object 202 is used for calibration of the light quantities. The calibration is performed using imaging signals obtained from the image capture. The reference object 202 is provided inside an end cap 203 removably attached to the distal portion 16a of the electronic endoscope 11. The end cap 203 is substantially cylindrical in shape and has an opening at one end and an enclosed surface at the other end. The insert section 16a is inserted into the opening. The reference object 202 is provided to the other end. The inner diameter of the end cap 203 is substantially the same as the outer diameter of the insert section 16a. Inside the end cap 203, a stopper (not shown) is provided. The stopper comes in contact with the insertion section 16a to restrict the insertion of the insert section 16a. When the end cap 203 is attached such that the stopper comes in contact with the insert section 16a, relative positional relations such as distances between the reference object 202 and the capture window 50 and the illumination window 49 disposed at an end surface of the distal end 16a and angles between the reference object 202, the capture window 50, and the illumination window 49 are set. Thus, by providing the reference object 202 inside the end cap 203, the imaging conditions, such as the distances and the angles, are fixed throughout the calibration. The end cap 203 is described by way of example. The reference object 202 may be provided in a member other than the end cap 203.

The calibration using the reference object 202 is performed as follows. First, before the shipping of the electronic endoscope system or at the regular maintenance, the first to third narrowband light sources 33 to 35 are set at normal light quantity ratios (the standard light quantity ratios). Then, an image of the reference object 202 is captured. An imaging signal ratio among the first to third narrowband imaging signals is stored as a standard imaging signal ratio in the internal memory (the RAM or the ROM) in the controller 59 in the processing apparatus 12. The standard imaging signal ratio includes a first standard brightness ratio and a second standard brightness ratio. The first standard brightness ratio is obtained when the first and third narrowband lights are applied to the reference object 202. The second standard brightness ratio is obtained when the second and third narrowband lights are applied to the reference object 202.

For example, prior to the examination using the electronic endoscope system 200, an image of the reference object 202 is captured again with the illumination of the first to third narrowband lights N1 to N3. Thereby, first to third calibration imaging signals are obtained. The difference value calculator 55c in the DSP 55 compares the imaging signal ratio of the first to third calibration imaging signals to the standard imaging signal ratio stored in the RAM to calculate a difference value that represents a difference between the imaging signal ratio and the standard imaging signal ratio.

The difference value between the imaging signal ratio and the standard imaging signal ratio is stored in a difference value memory 55d in the DSP 55. The difference value is also stored in the difference value storage 42a. During an examination using the electronic endoscope 11, the light source controller 42 controls the light quantities of the first to third narrowband lights N1 to N3 based on the difference value stored in the difference value storage 42a. The signal correcting section 55a in the DSP 55 corrects the first to third narrowband imaging signals based on the difference value stored in the difference value memory 55d.

In the fourth embodiment, both the light quantity control and the signal correction are performed based on the difference value. Alternatively, one of the light quantity control and the signal correction may be performed as in the first embodiment.

In the above embodiments, the broadband light source emits the broadband light BB. Alternatively, the broadband light BB may be emitted without using the broadband light source. In this case, a fluorescent material may be provided at an exit end of the light guide. The broadband light BB is generated when the fluorescent material is exposed to the first to third narrowband lights N1 to N3.

In the above embodiments, the vessel depth and the oxygen saturation are determined using the first to third narrowband light sources. In addition, a fourth narrowband light source may be used. The fourth narrowband light source emits four narrowband light N4 in a wavelength range around 532 nm (for example, 530±10 nm). The first to fourth narrowband image data are generated upon application of the first to fourth narrowband lights N1 to N4. The vessel depth and the oxygen saturation may be determined based on the first to fourth narrowband image data. Since light reaches deeper in the objective tissue as the wavelength increases, the fourth narrowband light N4 having a longer wavelength than the second narrowband light N2 allows to obtain vascular information of a deeper blood vessel.

In this case, the brightness ratio calculator 60 determines the vascular region from the first to fourth narrowband image data. Similar to the first embodiment, the first and second brightness ratios S1/S3 and S2/S3 are obtained. Furthermore, a third brightness ratio S4/S3 between the third and fourth narrowband image data is obtained. Here, the brightness value S4 denotes the brightness value of a picture element in the fourth narrowband image data. The vessel depth-oxygen saturation calculator 62 obtains the vessel depth information and the oxygen saturation information corresponding to the first to third brightness ratios based on the correlation between the first to third brightness ratios S1/S3, S2/S3, and S4/S3, the vessel depth, and the oxygen saturation in the same sequence as that of the first embodiment. The correlation is obtained previously from an experiment or the like.

The image capture may not be performed with illumination of each of the first to fourth narrowband lights N1 to N4. Similar to the second and third embodiments, composite narrowband light in which some of the first to fourth narrowband lights N1 to N4 are combined may be used to reduce the number of frames. For example, an image is captured while the first narrowband light N1 and the fourth narrowband light N4 are applied to the body cavity simultaneously. Then, an image is captured while the second narrowband light N2 and the third narrowband light N3 are applied simultaneously. Thereby, the total of two frames of imaging signals is obtained.

The imaging signal obtained from the first image capture is composed of an imaging signal B1 and an imaging signal G1. The imaging signals B1 and G1 have the brightness values shown below. The imaging signal obtained from the second image capture is composed of an imaging signal B2 and an imaging signal G2. The imaging signals B2 and G2 have the brightness values shown below.

> imaging signal $B1$=brightness value $S1$ corresponding to first narrowband light $N1$+brightness value $S4$ corresponding to fourth narrowband light $N4$ > imaging signal $G1$=brightness value $S4$ corresponding to fourth narrowband light $N4$ > imaging signal $B2$=brightness value $S2$ corresponding to second narrowband light $N2$+brightness value $S3$ corresponding to third narrowband light $N3$ > imaging signal $G2$=brightness value $S2$ corresponding to second narrowband light $N2$ The second narrowband image data is generated from the imaging signal G2 having only the brightness value S2. The fourth narrowband image data is generated from the imaging signal G1 having only the brightness value S4. The first narrowband image data is generated by separating the brightness value S4 from the imaging signal B1 using the calculation B1−(constant)×G1. The constant is determined by an intensity ratio between the first narrowband light N1 and the fourth narrowband light N4. The second narrowband image data is generated by separating the brightness value S3 from the imaging signal B2 using the calculation B2−(constant)× G2. The constant is determined by an intensity ratio between the second narrowband light N2 and the third narrowband light N3.

In the above embodiments, the narrowband lights are used as the first to fourth illumination lights by way of example. The first to fourth illumination lights may not necessarily be the narrowband lights. As described above, the narrowband light is especially necessary in, for example, the blue region of the absorption spectrum of hemoglobin where an interval between the two isosbestic points is small and the absorbance varies sharply. The isosbestic point is where the absorbance of deoxyhemoglobin 70 and the absorbance of oxyhemoglobin 70 crosses with each other. When the interval between the two isosbestic points is large, for example, in a red region, the wavelength range of the illumination light may be increased accordingly.

The third narrowband light N3 with a wavelength range having an isosbestic point as the center wavelength is used by way of example. The third illumination light is used as the reference light for the comparison with the first, second, and fourth illumination lights. Accordingly, only a level of the brightness is necessary for the third illumination light. The isosbestic point may not be included in the wavelength range of the third illumination light. The third illumination light may not be narrowband light. For example, the third illumination light may have the same wavelength range as that of B, G, or R in the normal mode. The third illumination light may be the broadband light BB including all of the B, G, and R.

[Additional Remark]

The following configuration is obtained according to the embodiments of the present invention.

[Additional Remark 1]

An electronic endoscope system comprising:

an electronic endoscope having an image sensor for capturing an image of an objective tissue including a blood vessel;

an illumination section for applying a first illumination light and a second illumination light to the objective tissue, the first and second illumination lights having different wavelength ranges from each other, each of the first and second illumination lights varying in absorbance in accordance with oxygen saturation of hemoglobin in the blood vessel;

a controller for controlling light quantities of the first and second illumination lights based on a light quantity ratio between the first and second illumination lights;

a signal obtaining section for obtaining a first imaging signal and a second imaging signal, the first and second imaging signals being outputted from the image sensor in accordance with respective reflection light quantities of reflection lights from the objective tissue upon application of the first and second illumination lights; and a vascular information obtaining section for obtaining vascular information based on the first and second imaging signals, the vascular information including both oxygen saturation information and vessel depth information.

[Additional Remark 2]

An electronic endoscope system comprising:

an electronic endoscope having an image sensor for capturing an image of an objective tissue including a blood vessel;

an illumination section for applying a first illumination light and a second illumination light to the objective tissue, the first and second illumination lights having different wavelength ranges from each other, each of the first and second illumination lights varying in absorbance in accordance with oxygen saturation of hemoglobin in the blood vessel;

a signal obtaining section for obtaining a first imaging signal and a second imaging signal, the first and second imaging signals being outputted from the image sensor in accordance with respective reflection light quantities of reflection lights from the objective tissue upon application of the first and second illumination lights;

a signal correcting section for correcting the first and second imaging signals based on a light quantity ratio between the first and second illumination lights; and a vascular information obtaining section for obtaining vascular information based on the first and second imaging signals, the vascular information including both oxygen saturation information and vessel depth information.

[Additional Remark 3]

A method for obtaining vascular information comprising the steps of:

applying first and second illumination lights to an objective tissue including a blood vessel, the first and second illumination lights having different wavelength ranges from each other, each of the first and second illumination lights varying in absorbance in accordance with hemoglobin oxygen saturation in the blood vessel;

controlling light quantities of the first and second illumination lights based on a light quantity ratio between the first and second illumination lights;

obtaining a first imaging signal and a second imaging signal, the first and second imaging signals being outputted from the image sensor in accordance with respective reflection light quantities of reflection lights from the objective tissue upon application of the first and second illumination lights;

obtaining vascular information based on the first and second imaging signals, the vascular information including both oxygen saturation information and vessel depth information.

[Additional Remark 4]

A method for obtaining vascular information comprising the steps of:

applying first and second illumination lights to an objective tissue including a blood vessel, the first and second illumination lights having different wavelength ranges from each other, each of the first and second illumination lights varying in absorbance in accordance with hemoglobin oxygen saturation in the blood vessel;

controlling light quantities of the first and second illumination lights based on a light quantity ratio between the first and second illumination lights;

obtaining a first imaging signal and a second imaging signal, the first and second imaging signals being outputted from the image sensor in accordance with respective reflection light quantities of reflection lights from the objective tissue upon application of the first and second illumination lights;

correcting the first and second imaging signals based on a light quantity ratio between the first and second illumination lights; and obtaining vascular information based on corrected first and second imaging signals, the vascular information including both oxygen saturation information and vessel depth information.

Various changes and modifications are possible in the present invention and may be understood to be within the present invention.

What is claimed is:

1. An electronic endoscope system comprising:

an electronic endoscope having an image sensor for capturing an image of an objective tissue including a blood vessel;

an illumination section for applying first to third illumination lights to the objective tissue, the first and second illumination lights having different wavelength ranges from each other, each of the first and second illumination lights varying in absorbance in accordance with oxygen saturation of hemoglobin in the blood vessel, the third illumination light being a reference light used for comparison with the first and second illumination lights;

a controller for controlling light quantities of the first to third illumination lights based on a first light quantity ratio between the light quantities of the first and third illumination lights and a second light quantity ratio between the light quantities of the second and third illumination lights;

a signal obtaining section for obtaining a first imaging signal, a second imaging signal, and a third imaging signal, the first to third imaging signals being outputted from the image sensor in accordance with respective reflection light quantities of reflection lights from the objective tissue upon application of the first to third illumination lights;

a vascular information obtaining section for obtaining vascular information based on a first brightness ratio and a second brightness ratio, the first brightness ratio being a ratio between the first and third imaging signals, the second brightness ratio being a ratio between the second and third imaging signals, the vascular information having both oxygen saturation information of the oxygen saturation and vessel depth information of the blood vessel.

2. The electronic endoscope system of claim 1, further including a light quantity detector for detecting light quantities of the first to third illumination lights, and wherein the controller controls the light quantities of the first to third illumination lights based on detected light quantities such that the first and second light quantity ratios reach respective standard light quantity ratios.

3. The electronic endoscope system of claim 2, further including a memory for storing the light quantities of the first to third illumination light and first to third image data, the light quantities of the first and third illumination lights being associated with the first to third image data, respectively, the first to third image data being generated based on the first to third imaging signals, respectively.

4. The electronic endoscope system of claim 1, wherein the first and second illumination lights are narrowband lights in a blue region.

5. The electronic endoscope system of claim 4, wherein at least one of the first and second illumination lights has a center wavelength at or below 450 nm.

6. The electronic endoscope system of claim 5, wherein in each of the wavelength ranges of the first and second illumination lights, magnitude relation between absorbance of deoxyhemoglobin and absorbance of oxyhemoglobin is reversed in respective absorption spectra.

7. The electronic endoscope system of claim 6, wherein the wavelength range of the first illumination light is 440±10 nm and the wavelength range of the second illumination light is 470±10 nm.

8. The electronic endoscope system of claim 1, further including a calibration imaging signal obtaining section for obtaining first to third calibration imaging signals outputted from the image sensor in accordance with respective reflection light quantities of lights reflected by a reference object upon application of the first to third illumination lights, the reference object having a known reflection spectrum;

a difference value storage for storing a difference value between a first imaging signal ratio and its corresponding standard imaging signal ratio and a difference value between the second imaging signal ratio and its corresponding standard imaging signal ratio, the difference values being calculated based on the first and second imaging signal ratios, the first imaging signal ratio being a ratio between the first and third calibration imaging signals and corresponding to the first light quantity ratio, the second imaging signal ratio being a ratio between the second and third calibration imaging signals and corresponding to the second light quantity ratio;

and wherein the controller controls the light quantities of the first to third illumination lights based on the difference values.

9. An electronic endoscope system comprising:
an electronic endoscope having an image sensor for capturing an image of an objective tissue including a blood vessel;
an illumination section for applying a first illumination light, a second illumination light, and a third illumination light to the objective tissue, the first and second illumination lights having different wavelength ranges from each other, each of the first and second illumination lights varying in absorbance in accordance with oxygen saturation of hemoglobin in the blood vessel, and a third illumination light being a reference light used for comparison with the first and second illumination lights;
a signal obtaining section for obtaining a first imaging signal, a second imaging signal, and a third imaging signal, the first to third imaging signals being outputted from the image sensor in accordance with respective reflection light quantities of reflection lights from the objective tissue upon application of the first to third illumination lights;
a signal correcting section for correcting the first to third imaging signals based on a first light quantity ratio between the light quantities of the first and third illumination lights and a second light quantity ratio between the light quantities of the second and third illumination lights; and
a vascular information obtaining section for obtaining vascular information based on a first brightness ratio and a second brightness ratio, the first brightness ratio being a ratio between a corrected first imaging signal and a corrected third imaging signal, the second brightness ratio being a ratio between a corrected second imaging signal and a corrected third imaging signal, the vascular information having both oxygen saturation information of the oxygen saturation and vessel depth information of the blood vessel.

10. The electronic endoscope system of claim 9, further including a light quantity detector for detecting the light quantities of the first to third illumination lights, and the signal correcting section correcting the first to third imaging signals based on a difference value between the first light quantity ratio and its corresponding standard light quantity ratio and a difference value between the second light quantity ratio and its corresponding standard light quantity ratio, and the difference values are calculated based on the light quantities detected by the light quantity detector, and the vascular information obtaining section obtains the vascular information based on the corrected first to third imaging signals.

11. The electronic endoscope system of claim 9, further including:
a calibration imaging signal obtaining section for obtaining first to third calibration imaging signals outputted from the image sensor in accordance with respective reflection light quantities of lights reflected by a reference object upon application of the first to third illumination lights, the reference object having a known reflection spectrum;
a difference value memory for storing a difference value between a first imaging signal ratio and its corresponding standard imaging signal ratio and a difference value between the second imaging signal ratio and its corresponding standard imaging signal ratio, the difference values being calculated based on the first and second imaging signal ratios, the first imaging signal ratio being a ratio between the first and third calibration imaging signals and corresponding to the first light quantity ratio, the second imaging signal ratio being a ratio between the second and third calibration imaging signals and corresponding to the second light quantity ratio;

and wherein the signal correcting section corrects the first to third imaging signals based on the difference values and the vascular information obtaining section obtains the vascular information based on corrected first to third imaging signals.

12. A method for obtaining vascular information comprising the steps of:
applying first to third illumination lights to an objective tissue having a blood vessel, the first and second illumination lights having different wavelength ranges from each other, each of the first and second illumination lights varying in absorbance in accordance with oxygen saturation of hemoglobin in the blood vessel, the third illumination light being a reference light used for comparison with the first and second illumination lights;
controlling light quantities of the first to third illumination lights based on a first light quantity ratio between light quantities of the first and third illumination lights and a second light quantity ratio between light quantities of the second and third illumination lights;
obtaining first to third imaging signals outputted from the image sensor in accordance with respective reflection light quantities of lights reflected by the objective tissue upon application of the first to third illumination lights;
obtaining vascular information based on a first brightness ratio and a second brightness ratio, the first brightness ratio being a ratio between signal values of the first imaging signal and the third imaging signal, the second brightness ratio being a ratio between signal values of the second imaging signal and the third imaging signal, the vascular information having both oxygen saturation information of the oxygen saturation and vessel depth information of the blood vessel.

13. The method for obtaining the vascular information of claim 12, further including the step of detecting light quantities of the first to third illumination lights; and
wherein the light quantities of the first to third illumination lights are controlled such that the first light quantity ratio and the second light quantity ratio reach their respective standard light quantity ratios during the light quantity control.

14. The method for obtaining the vascular information of claim 12, further including the steps of:
obtaining first to third calibration imaging signals outputted from the image sensor in accordance with respective reflection light quantities of lights reflected by a reference object upon application of the first to third illumination lights, the reference object having a known reflection spectrum; and
storing a difference value between a first imaging signal ratio and its corresponding standard imaging signal ratio and a difference value between the second imaging signal ratio and its corresponding standard imaging signal ratio, the difference values being calculated based on the first and second imaging signal ratios, the first imaging signal ratio being a ratio between the first and third calibration imaging signals and corresponding to the first light quantity ratio, the second imaging signal ratio being a ratio between the second and third calibration imaging signals and corresponding to the second light quantity ratio; and wherein the light quantities of the first to third light quantities of the illumination lights are controlled based on the difference values during the light quantity control of the first to third illumination lights.

15. A method for obtaining vascular information comprising the steps of:

applying first to third illumination lights to an objective tissue having a blood vessel, the first and second illumination lights having different wavelength ranges from each other, each of the first and second illumination lights varying in absorbance in accordance with oxygen saturation of hemoglobin in the blood vessel, the third illumination light being a reference light used for comparison with the first and second illumination lights;

obtaining first to third imaging signals outputted from the image sensor, the first to third imaging signals corresponding to respective reflection light quantities of reflection lights from the objective tissue upon application of the first and second illumination lights;

correcting the first to third imaging signals based on a first light quantity ratio and a second light quantity ratio, the first light quantity ratio being a ratio between light quantities of the first and third illumination lights, the second light quantity ratio being a ratio between light quantities of the second and third illumination lights;

obtaining vascular information based on a first brightness ratio and a second brightness ratio, the first brightness ratio being a ratio between signal values of a corrected first imaging signal and a corrected third imaging signal, the second brightness ratio being a ratio between signal values of a corrected second imaging signal and the corrected third imaging signal, the vascular information having both oxygen saturation information of the oxygen saturation and vessel depth information of the blood vessel.

16. The method for obtaining vascular information of claim 15, further including the steps of:

detecting the light quantities of the first to third illumination lights; and wherein the first to third imaging signals are corrected based on a difference value between the first light quantity ratio and its corresponding standard light quantity ratio and a difference value between the second light quantity ratio and its corresponding standard light quantity ratio, the difference values being calculated based on the detected light quantities.

17. The method for obtaining vascular information of claim 15, further comprising the step of:

obtaining first to third calibration imaging signals outputted from the image sensor in accordance with respective reflection light quantities of lights reflected by a reference object upon application of the first to third illumination lights, the reference object having a known reflection spectrum;

storing a difference value between a first imaging signal ratio and its corresponding standard imaging signal ratio and a difference value between the second imaging signal ratio and its corresponding standard imaging signal ratio, the difference value being calculated based on the first and second imaging signal ratios, the first imaging signal ratio being a ratio between the first and third calibration imaging signals and corresponding to the first light quantity ratio, the second imaging signal ratio being a ratio between the second and third calibration imaging signals and corresponding to the second light quantity ratio; and wherein the first to third imaging signals are corrected based on the difference values in the correction of the first to third imaging signals.

* * * * *